US008536323B2

(12) United States Patent
Opperman et al.

(10) Patent No.: US 8,536,323 B2
(45) Date of Patent: Sep. 17, 2013

(54) MODIFIED NUCLEOTIDES

(75) Inventors: Kay Opperman, Rockton, IL (US);
Barbara J. Kaboord, Oregon, WI (US);
Jean-Samuel Schultz, Rockford, IL (US); Christopher L. Etienne, Fitchburg, WI (US); Greg Hermanson, Loves Park, IL (US)

(73) Assignee: Pierce Biotechnology, Inc., Rockford, IL (US)

( * ) Notice: Subject to any disclaimer, the term of this patent is extended or adjusted under 35 U.S.C. 154(b) by 280 days.

(21) Appl. No.: 13/090,729

(22) Filed: Apr. 20, 2011

(65) Prior Publication Data
US 2011/0262917 A1 Oct. 27, 2011

Related U.S. Application Data

(60) Provisional application No. 61/326,450, filed on Apr. 21, 2010.

(51) Int. Cl.
*C07H 19/067* (2006.01)
*C07H 19/167* (2006.01)

(52) U.S. Cl.
CPC ............ *C07H 19/067* (2013.01); *C07H 19/167* (2013.01)
USPC ........................................................ 536/26.3

(58) Field of Classification Search
None
See application file for complete search history.

(56) References Cited

U.S. PATENT DOCUMENTS

| | | | |
|---|---|---|---|
| 4,914,210 A | 4/1990 | Levenson et al. | |
| 5,047,519 A | 9/1991 | Hobbs, Jr. et al. | |
| 5,151,507 A | 9/1992 | Hobbs, Jr. et al. | |
| 5,247,081 A | 9/1993 | Edge | |
| 5,558,991 A | 9/1996 | Trainor | |
| 5,567,811 A | 10/1996 | Misura et al. | |
| 5,608,063 A | 3/1997 | Hobbs, Jr. et al. | |
| 5,684,142 A | 11/1997 | Mishra et al. | |
| 5,888,819 A | 3/1999 | Goelet et al. | |
| 5,952,174 A | 9/1999 | Nikiforov et al. | |
| 6,004,744 A | 12/1999 | Goelet et al. | |
| 6,013,431 A | 1/2000 | Sodelund et al. | |
| 6,114,350 A | 9/2000 | Randall et al. | |
| 6,197,956 B1 | 3/2001 | Randall et al. | |
| 6,204,389 B1 | 3/2001 | Randall et al. | |
| 6,224,644 B1 | 5/2001 | Randall et al. | |
| 7,361,465 B2 | 4/2008 | Murphy et al. | |
| 7,491,818 B2 | 2/2009 | McGall et al. | |
| 7,504,215 B2 | 3/2009 | Cole et al. | |
| 7,524,942 B2 | 4/2009 | Wang et al. | |
| 7,541,144 B2 | 6/2009 | Wang | |
| 7,572,585 B2 | 8/2009 | Wang | |
| 2003/0165849 A1* | 9/2003 | Zhang et al. ............ | 435/6 |
| 2008/0045418 A1 | 2/2008 | Xia | |
| 2009/0176732 A1 | 7/2009 | Beigelman et al. | |
| 2009/0286753 A1 | 11/2009 | Kauppinen et al. | |

FOREIGN PATENT DOCUMENTS

WO 2004/052907 6/2004

OTHER PUBLICATIONS

Hall-Pogar, et al. Specific *trans*-acting proteins interact with auxiliary RNA polyadenylation elements in the COX-2 3'-UTR. *RNA* (2007), 13:1103-1115, Cold Spring Harbor Laboratory Press.
O'Connor, et al. Two Purified Domains of Telomerase Reverse Transcriptase Reconstitute Sequence-specific Interactions with RNA. *The Journal of Biological Chemistry*, vol. 280, No. 17, Apr. 29, pp. 17533-17539, 2005.
Ueda, C.T. and Roberts, R.W. Analysis of a long-range interaction between conserved domains of human telomerase RNA. *RNA* 2004 10: 139-147, pp. 139-147.
Leibold, E.A. and Munro, H.N. Cytoplasmic protein binds in vitro to a highly conserved sequence in the 5' untranslated region of ferritin heavy- and light-subunit mRNAs. *Cell Biology*, vol. 85, pp. 2171-2175, Apr. 1988.
Piskounova, et al. Determinants of MicroRNA Processing Inhibition by the Developmentally.Regulated RNA-binding Protein Lin28. *Journal of Biological Chemistry*, vol. 283 No. 31 pp. 21310-21314, Aug. 1, 2008.
McKinley, B.A. and Sukhodolets, M.V. *Escherichia coli* RNA polymerase-associated SWI/SNF protein RapA: evidence for RNA-directed binding and remodeling activity. *Nucleic Acids Research*, 2007, vol. 35, No. 21, pp. 7044-7060, Oct. 2, 2007.
Sukhodolets, M.V. and Ding, J.J. RapA, A Novel RNA Polymerase-Associated Protein, Is a Bacterial Homolog of SWI2/SNF2. *The Journal of Biological Chemistry*, vol. 273, No. 12, pp. 7018-7023, Mar. 20, 1998.
England, T.E., et al. Dinucleoside pyrophosphates are substrates for T4-induced RNA ligase. *Proc. Natl. Acad. Sci. USA, Biochemistry*, vol. 74, No. 11, pp. 4839-4842, Nov. 1977.
Hinton, D.M., et al. The preparative synthesis of oligodeoxyribonucleotides using RNA ligase. *Nucleic Acids Research*, vol. 10, No. 6, pp. 18771894, 1982.
Romaniuk, E., et al. The Effect of Acceptor Oligoribonucleotide Sequence on the $T_4$ RNA Ligase Reaction. *Eur. J. Biochem*, 125, 639-643 (1982).
Richardson, Ross W. and Gumport, Richard I. Biotin and fluorescent labeling of RNA using T4 RNA ligase. *Nucleic Acids Research*, vol. 11, No. 18, pp. 6167-6184, 1983.
Walker, G.C., et al. T4-Induced RNA Ligase Joins Single-Stranded Oligoribonucleotides. *Proc. Nat. Acad. Sci. USA*, vol. 72, No. 1, pp. 122-126, Jan. 1975.
Brennan, Catherine A. and Gumport, Richard I. T4 RNA ligase catalyzed synthesis of base analogue-containing oligodeoxyribonucleotides and a characterization of their thermal stabilities. *Nucleic Acids Research*, vol. 13, No. 24, pp. 8665-8684, 1985.
England, TE, Bruce, AG, and OC Uhlenbeck. Specific labeling of 3' termini of RNA with T4 RNA ligase (1980) *Methods Enzym*. 65: 65-74.
G Keith. Optimization of conditions for labeling the 3' OH end of tRNA using T4 RNA ligase. (1983) *Biochimie* 65: 367-70.
Romaniuk, E. et al., Joining of RNA molecules with RNA ligase (1983) Methods Enzym 100: 52-59.
Hobbs, F. W. Jr. Palladium-Catalyzed Synthesis of Alkynylamino Nucleosides. A Universal Linker for Nucleic Acids. (1989) J. Org. Chem 54(14): 3420-3422.
Lee, S.E. et al., Enhancing the catalytic reopertoire of nucleic acids: a systematic study of length and rigidity (2001) Nucleic Acids Res. 29(7): 1565-1573.

(Continued)

*Primary Examiner* — Eric S Olson
(74) *Attorney, Agent, or Firm* — Thompson Hine LLP

(57) ABSTRACT

Modified nucleotides, and methods to modify nucleotides with a moiety or label, such as biotin, that permits their detection and results in a modified nucleotide, and methods of use of the modified nucleotide in quantitative and qualitative assays.

20 Claims, 7 Drawing Sheets

(56) References Cited

OTHER PUBLICATIONS

Langer, P. R. et al., Enzymatic synthesis of biotin-labelled polynucleotides: novel nucleic acid affinity probes. (1981) PNAS 78(11): 6633-6637.

Cole, K. et al., Direct labeling of RNA with multiple biotins allows sensitive expression profiling of acute leukemia class predictor genes (2004) Nucleic Acids Res 32(11); e86.

United Kingdom Search Report, GB1106948.1, search date of Jul. 28, 2011, 3 pages.

Barone et al. Novel Nucleoside Triphosphate Analogs for the Enzymatic Labeling of Nucleic Acids in *Nucleosides, Nucleotides & Nucleic Acids*, 20(4-7), 1141-1145 (2001).

Extended European Search Report, EP 12187509.0, mailed Jun. 4, 2013 (8 pages).

(D2) Gomes and Gozzo. Chemical cross-linking with a diazirine photoactivatable cross-linker investigated by MALDI- and ESI-MS/MS. J. Mass Spectrom. vol. 45 (2010), pp. 892-899.

(D3) Shigdel et al. Diazirine-Based DNA Photo-Cross-Linking Probes for the Study of Protein-DNA Interactions. Angew. Chem. Int. Ed. vol. 47 (2008), pp. 90-93.

(D4) Hanna et al. Synthesis and characterization of a new photocrosslinking CTP analog and its use in photoaffinity labeling *E.coli* and T7 RNA polymerases. Nucleic Acids Research, vol. 21, No. 9 (1993), pp. 2073-2079.

\* cited by examiner

Preparation of Biotin-PEG$_4$-Alkane-3′, 5′-Cytidine Bisphosphate

Synthesis of Biotin-Linker-Alkyne-3´, 5´-Cytidine Bisphosphate

Synthesis of Biotin Linker-Alkene-3´, 5´-Cytidine Bisphosphate

Nucleotide Alkyne Linkage Reactivity in Cell Extracts

3',5'-Bisphosphorylated Cytidine-Alkyne-LC-Biotin

Nucleotide Alkene Linkage Reactivity in Cell Extract

3',5'-Bisphophorylated Cytidine-Alkene-LC-Biotin

```
                           SEQUENCE LISTING

<160> NUMBER OF SEQ ID NOS: 2

<210> SEQ ID NO 1
<211> LENGTH: 27
<212> TYPE: RNA
<213> ORGANISM: Artificial Sequence
<220> FEATURE:
<223> OTHER INFORMATION: Artificial oligonucleotide

<400> SEQUENCE: 1
uccugcuuca acagugcuug gacggaa                                          27

<210> SEQ ID NO 2
<211> LENGTH: 43
<212> TYPE: RNA
<213> ORGANISM: Artificial Sequence
<220> FEATURE:
<223> OTHER INFORMATION: Artificial oligonucleotide

<400> SEQUENCE: 2
ccugguuuuu aaggaguguc gccagagugc cgcgaaugaa aaa                        43
```

MODIFIED NUCLEOTIDES

This application claims priority from U.S. Provisional application Ser. No. 61/326,450, filed Apr. 21, 2010, which is expressly incorporated by reference herein in its entirety.

Modified nucleotides, methods to modify nucleotides with a moiety or label, such as biotin, that permit their detection and result in a modified nucleotide, methods of use of the modified nucleotide in quantitative and qualitative assays, and methods of synthesizing the disclosed modified nucleotides.

The modified nucleotides have the structure P1-P2-Nus-Alk-Lnk-Obs, and include a salt, conjugate base, tautomer, or ionized form, where P1 is a phosphate group; P2 is a phosphate group; Nus is a nucleoside moiety comprising a sugar bound to a purine or pyrimidine base; Alk is a connecting group having the structure —//—$(CH_2)_m$—Y—//— where Y is a bond or bond forming group selected from

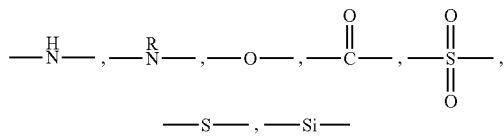

and
m is an integer ranging from 3 to 6 inclusive, and where the leftmost bond is to Nus and the rightmost bond is to Lnk; Lnk is a linking group having the structure

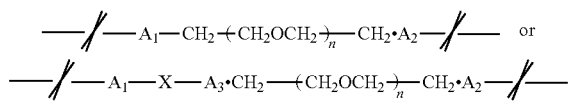

where n is an integer ranging from 2 to 48 inclusive; $A_1$ is a bond forming group selected from

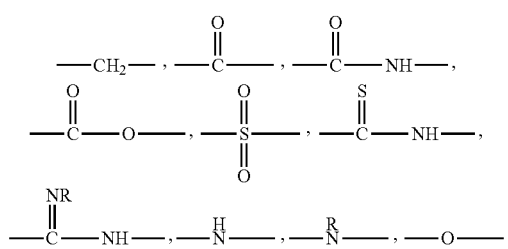

$A_2$ is a bond forming group selected from

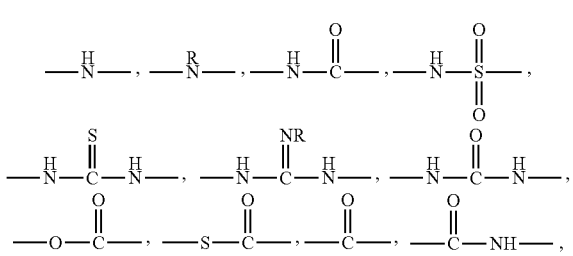

$A_3$, when present, is a bond forming group selected from

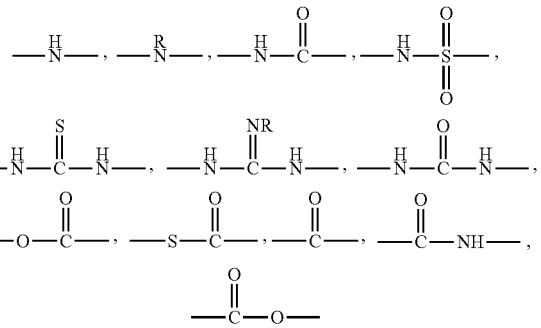

X is a cleavable group that can undergo silicon-carbon cleavage, nucleophilic cleavage, redox cleavage, photochemical cleavage, enzymatic cleavage, or exchange-based cleavage, and
the leftmost bond is to Alk and the rightmost bond is to Obs; and Obs is an observable label moiety.

Such modified nucleotides, also termed nucleotide analogs, retain biological activity. For example, they are substrates for a variety of DNA and/or RNA polymerases. The modified nucleotide is added to an oligonucleotide or nucleic acid by routine methods, e.g., nick translation, random priming, polymerase chain reaction (PCR), 3'-end labeling, transcribing RNA using SP6, T3, or T7 RNA polymerases, etc.

Modified nucleotides may be used to form labeled probes that may be used in, e.g., biological screening, diagnosis, etc. As one example, screening an array permits different constituents of a complex sample to be determined. For example, an oligonucleotide probe containing a biotinylated nucleotide specifically binds to analytes in the sample that contain a complementary sequence, yielding an observable binding pattern detectable upon interrogating the array. As another example, an oligonucleotide probe containing a biontinylated nucleotide can be used to investigate small ribonucleic acids (RNAs) such as microRNAs (miRNAs), and their functional interactions with other RNA molecules or cellular proteins.

Figure 1:
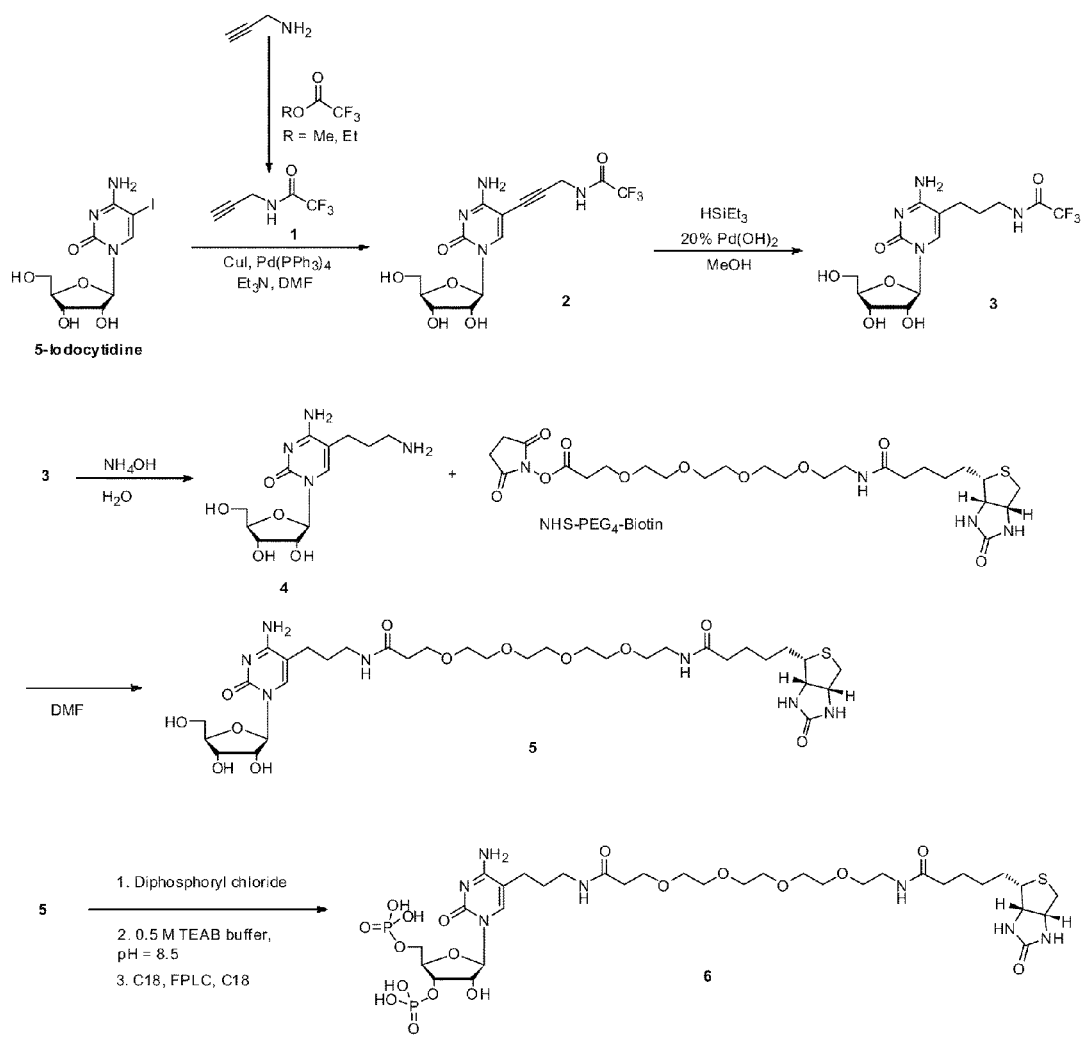
FIG. 1 shows synthesis of biotin-polyethylene glycol (PEG)-alkane-3',5'-cytidine bisphosphate.

As subsequently disclosed, the nucleotide can be modified by adding at least one of the following substituents that function as detector molecules, either directly or indirectly: biotin and derivatives, azide, alkyne, aldehyde, diene, amine, disulfide, fluorophore, spin label, polyethyleneglycol (PEG). These substituents are added in various permutations, specific entities, and chain lengths.

In one embodiment, the modified nucleotide is a biotinylated nucleotide having the formula biotin-polyethylene glycol (PEG)-alkane-nucleotide with PEG having at least 7 carbon atoms and up to 100 carbon atoms. For any of the disclosed inventive compounds, the compound includes the salt form, conjugate base, tautomer, and/or ionized form. In one embodiment, the modified nucleotide is a ribonucleotide. In one embodiment, the ribonucleotide can be, but is not limited to, cytidine.

In one embodiment, the biotinylated nucleotide is a cytidine 3'-5'-bisphosphate having a $PEG_4$ linker with the structure shown below.

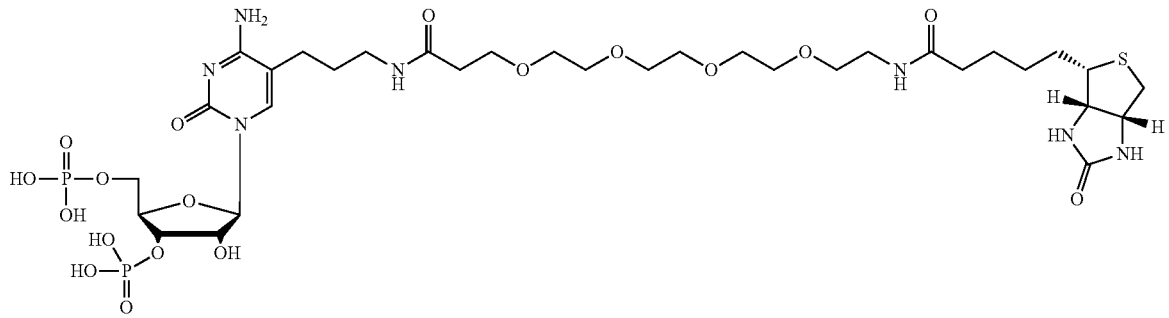

This structure had enhanced ligation efficiency over prior art biotinylated compounds due to the presence of the alkane adjacent to cytidine.

One embodiment is a method for labeling an RNA probe with a biotinylated nucleotide having the structure

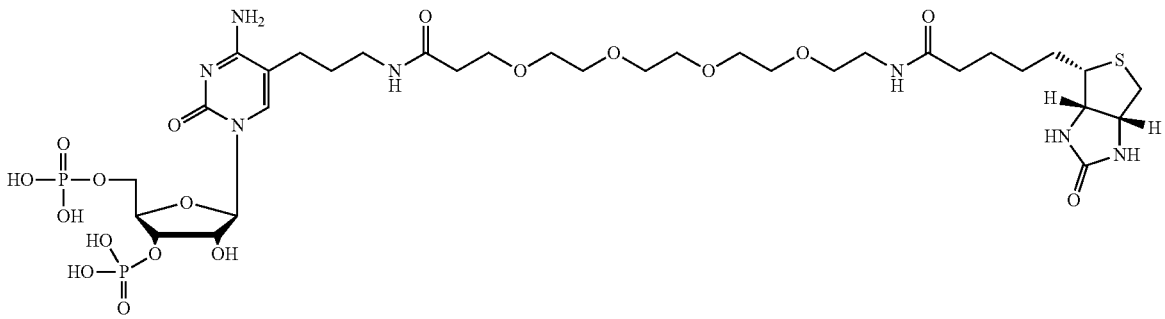

under conditions that label the RNA probe. The modified ribonucleotide is incubated with an enzyme capable of ligating the biotinylated ribonucleotide to the RNA probe (e.g., a ligase such as T4 ligase), to result in a biotin-labeled RNA probe. In one embodiment, single stranded T4 ligase is used. In one embodiment, double stranded T4 ligase is used. In one embodiment, thermostable T4 ligase is used. Examples of suitable ligases include T4 RNA Ligase 1 (applications include labeling of 3'-termini of RNA with 5'-[$^{32}$P] pCp, inter- and intramolecular joining of RNA and DNA molecules; synthesis of single-stranded oligodeoxyribonucleotides; and incorporation of unnatural amino acids into proteins); T4 RNA Ligase 2 (applications include ligating a nick in dsRNA, splintered RNA ligation, and ligating the 3' OH of RNA to the 5' phosphate of DNA in a double stranded structure); T4 RNA Ligase 2, truncated (applications include joining a single stranded adenylated primer to RNAs for cloning, and small RNA cloning); T4 RNA Ligase 2, truncated K227Q (applications include joining a single stranded adenylated primer to RNAs for cloning, small RNA cloning, and ligating with the lowest possible ligation byproduct); each of which is commercially available from New England BioLab; and thermostable RNA ligase, which is able to perform ligations at elevated temperatures, such as above about 40°, commercially available from Epicentre. In one embodiment, the modified nucleotide is purified prior to ligation. Subsequent assaying for the biotinylated probe permits detection of the presence, quantity, etc. of the ribonucleotide in the sample. The method is used with, e.g., and without limitation, mobility shift assays, Northern blots, in situ hybridization, etc. Biotin-labeled RNA probe can be detected using a streptavidin-conjugated reporter molecule such as, e.g. and without limitation, enzymes (e.g., peroxidases), fluorescent dyes, etc.

One embodiment is a method of synthesizing biotin-PEG-4-alkane-3',5'-cytidine-bisphosphate.

One embodiment is a kit containing a compound having the structure

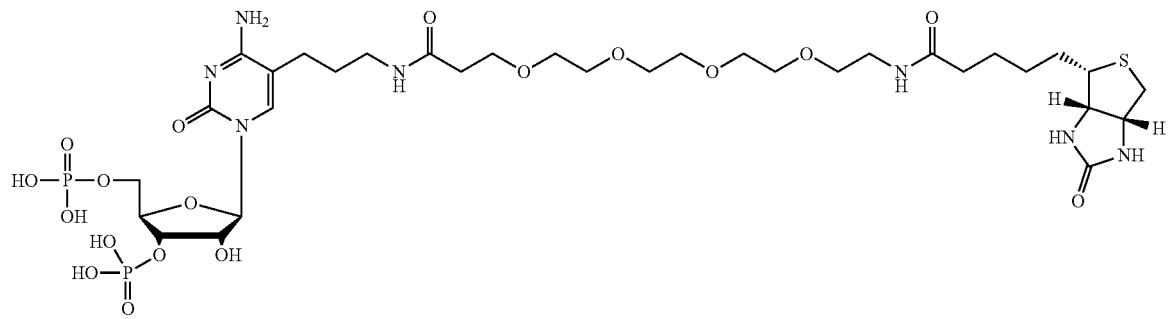

and instructions for labeling a nucleic acid using the compound. The kit can also contain an enzyme, a control RNA (either labeled or unlabeled with the modified nucleotide), and buffer.

The modified nucleotide has enhanced ligation efficiency over known compounds due to the presence of an alkane linkage. The alkane linkage also improves functionality of the modified nucleotide by decreasing reactivity of the modified nucleotide with cell lysates. The PEG spacer increases hydrophilicity of the modified nucleotide to increase accessibility of the biotin for detection.

In one embodiment, the biotinylated nucleotide compounds have the following structure: P1-P2-Nus-Alk-Lnk-Obs (I) or its salt, conjugate base, tautomer, or ionized form where P1 and P2 are phosphate groups;

Nus is a nucleoside (a sugar (e.g., ribose) bound to a purine or pyrimidine base);

Alk is a connecting group that can be directly or indirectly bonded between Nus and Lnk, having the structure —//—(CH$_2$)$_m$—Y—//— in which Y is a bond forming group selected from

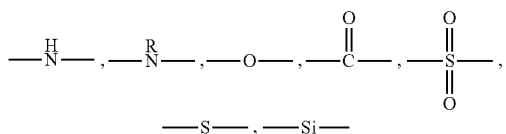

and m is an integer ranging from 3 to 6 inclusive, and the leftmost bond is to Nus and the rightmost bond is to Lnk;

Lnk is a linking group between Alk and Obs, having the following structures

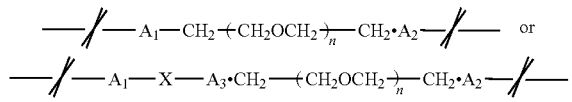

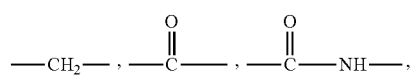

in which n is an integer ranging from 2 to 48 inclusive;

A$_1$ is a bond forming group selected from

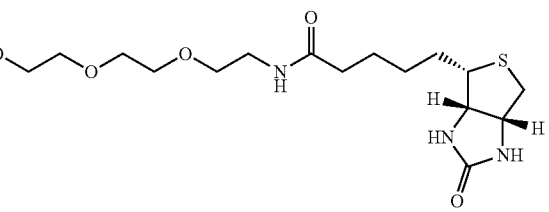

-continued

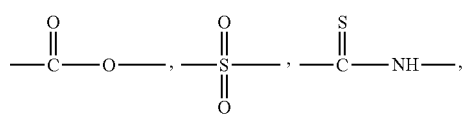

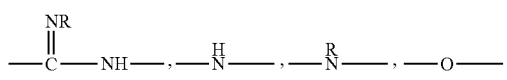

$A_2$ is a bond forming group selected from

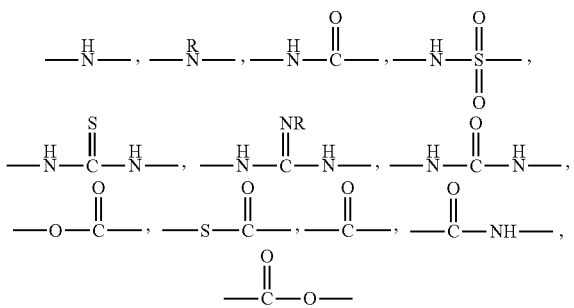

$A_3$ is a bond forming group selected from

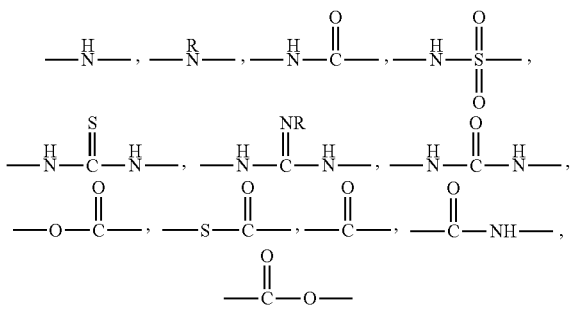

X is a cleavable group that can undergo silicon-carbon cleavage, nucleophilic cleavage, redox cleavage, photochemical cleavage, enzymatic cleavage, or exchange-based cleavage; and Obs is an observable label.

Y functions as a handle to permit attachment of detector molecules (e.g., fluorophore, biotin, etc)

When the sugar is ribose, it has the following attachments: P1 is attached at the 5' position; P2 is attached at the 3' position; and the purine or pyrimidine base is attached at the 1' position.

The purine or pyrimidine base is selected from cytosine (C), uracil (U), adenine (A), thymine (T), guanine (G), or inosine (I) and may be modified or unmodified. Embodiments include, but are not limited to, 1-methyladenine, N6-methyladenine, N6-isopentyladenine, N,N-dimethyladenine, 7-deazaadenine, 2-thiocytosine, 3-methylcytosine, N4-acetylcytosine, 2-thiocytosine, 1-methylguanine, 2-methylguanine, 7-methylguanine, N2,N2-dimethylguanine, 7-deazaguanine, 2-thiouracil, 6-thiopurine, or 2,6-diaminopurine.

The modification may be an observable label. Observable labels include, but are not limited to, a chromogenic moiety, a fluorophore such as fluorescein, rhodamine, a commercial dye (e.g., DyLight® (Dyomics), Alexa®, Cy3, Cy5), a mass label, a spin label, or a moiety capable of binding an observable label, such as a streptavidin-binding label such as biotin, desthiobiotin or iminobiotin, or a secondary detection label such as azide, alkyne, aldehyde, or diene, which are capable of forming a covalent bond with an alkyne, phosphine, azide, hydrazide, alkoxyamine, or alkene present on an observable label. In one embodiment, the observable label is biotin, and the compound is biotin-$PEG_4$-alkane-3',5'-cytidine-bisphosphate. In one embodiment, the observable label is an azide, and the compound is azido-$PEG_4$-alkane-3',5'-cytidine-bisphosphate. In one embodiment, the observable label is a fluorophore, and the compound is Cy5-$PEG_4$-alkane-3',5'-cytidine-bisphosphate. Labeling occurs with high efficiency and comparable sensitivity to radioisotope labeling, yet avoids the use of radioactivity with its concomitant disadvantages.

In one embodiment, n is an integer ranging from 2 to 24 inclusive, the sugar is ribose, the purine or pyrimidine base is A, C, G, U, or I, m is 3, n is 4, and the observable label is a streptavidin-binding label selected from biotin, desthiobiotin, or iminobiotin.

In one embodiment, the modified nucleotide compounds have the following structure (II):

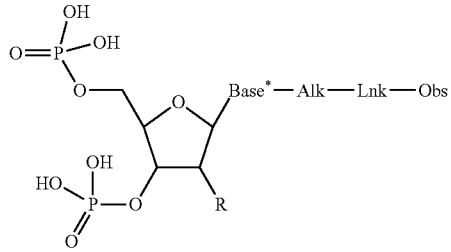

or its salt, conjugate base, tautomer, or ionized form where
Base* is a purine or pyrimidine base;
R is H, OH, $CH_3$, or a hydroxyl protecting group;
Alk is a connecting group between Base* and Lnk, having the structure —//—$(CH_2)_m$—Y—//— in which Y is a bond forming group selected from

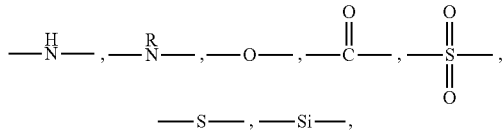

and
m is an integer ranging from 3 to 6 inclusive;
Lnk is a linking group having the following structures:

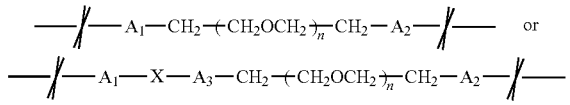

in which n is an integer ranging from 2 to 48 inclusive;
$A_1$ is a bond forming group selected from

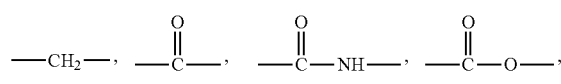

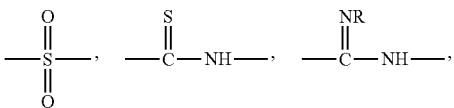

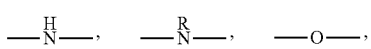

$A_2$ is a bond forming group selected from

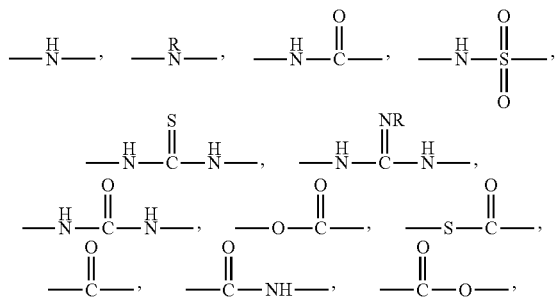

$A_3$ is a bond forming group selected from

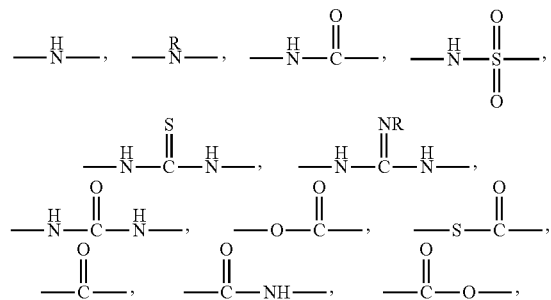

X is a cleavable group that can undergo silicon-carbon cleavage, nucleophilic cleavage, redox cleavage, acid cleavage, base cleavage, photochemical cleavage, enzymatic cleavage, or exchange-based cleavage;

Obs is an observable label moiety.

The sugar group may be ribose or deoxyribose. The purine or pyrimidine base is selected from C, U, A, G, T, or I and may be modified or unmodified. Embodiments include, but are not limited to, 1-methyladenine, N6-methyladenine, N6-isopentyladenine, N,N-dimethyladenine, 7-deazaadenine, 2-thiocytosine, 3-methylcytosine, N4-acetylcytosine, 2-thiocytosine, 1-methylguanine, 2-methylguanine, 7-methylguanine, N2,N2-dimethylguanine, 7-deazaguanine, 2-thiouracil, 6-thiopurine, or 2,6-diaminopurine.

The observable label may be a chromogenic moiety, a fluorophore such as fluorescein, rhodamine, a commercial dye (e.g., DyLight® (Dyomics), Alexa®, Cy3, Cy5), a mass label, a spin label, or a moiety capable of binding an observable label, such as a streptavidin-binding label such as biotin, desthiobiotin or iminobiotin, or a secondary detection label such as azide, alkyne, aldehyde, or diene.

In one embodiment, n is an integer ranging from 2 to 24 inclusive. In one embodiment, the sugar is ribose, the purine or pyrimidine base is A, C, G, U, or I, m is 3, n is 4, and the observable label is a streptavidin-binding label selected from biotin, desthiobiotin, or iminobiotin.

In one embodiment, the sugar is ribose, the purine or pyrimidine base is C, m is 3, Lnk is

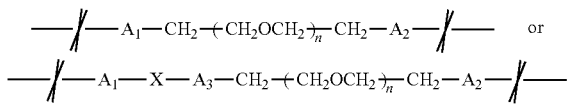

n is 4, $A_1$ is

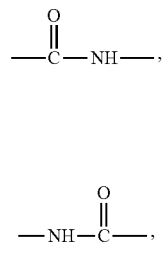

$A_2$ is

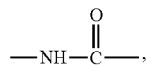

and when present, $A_3$ is

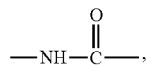

and Obs is selected from the group consisting of biotin, a fluorophore, and an azide.

One embodiment is a method of labeling RNA by heating the desired RNA sample to at least 75° C. up to 95° C. In one embodiment, the solution containing the RNA sample contained dimethylsulfoxide (DMSO) at a concentration ranging from 0% to 25%. The RNA sample was heated for 1 minute to 5 minutes, then rapidly cooled on ice to between 2° C. and 10° C. for at least one minute. The RNA then was contacted with one of the modified nucleotide compounds having the structure P1-P2-Nus-Alk-Lnk-Obs as described above. The nucleotide was ligated to the RNA to result in a labeled RNA.

The modified nucleotide was ligated to the RNA using an enzyme such as, but not limited to, T4 RNA ligase, to result in a labeled RNA. In this embodiment, RNA was heated to at least 75° C., and up to 95° C., then cooled for at least one minute to less than 10° C. The cooled RNA was then contacted with the biotinylated cytidine bisphosphate under reaction conditions using T4 RNA ligase and including PEG having molecular weight between about 1500 and 24,000 inclusive and at a concentration ranging from 5% PEG to 20% PEG inclusive. The reaction was incubated between 30 minutes and 16 hours at temperature ranging between 16° C. and 37° C. to ligate the biotinylated cytidine bisphosphate to the RNA, resulting in a modified RNA.

Synthesis of exemplary specific compounds among each of the following modified nucleotides is subsequently described. One skilled in the art will appreciate that such synthesis schemes are representative and not limiting; one skilled in the art will know how to synthesize other specific examples using known methods and without undue experimentation. They include, but are not limited to: biotin-PEG$_4$ modifications: overview of biotin-PEG$_4$-alkane-3',5'-cytidine-bisphosphate (BPA-3',5'-pCp, compound 6), overview of biotin-PEG$_4$-SS-alkane-3',5'-cytidine-bisphosphate (BP$_4$SSA-3',5'-pCp, compound 12), biotin-PEG$_4$-SS-alkane-cytidine (BP$_4$SSAC, compound 11), and detailed reactions for biotin-PEG$_4$-SS-alkane-3',5'-cytidine-bisphosphate (BP$_4$SSA-3',5'-pCp, compound 12); biotin-PEG$_{12}$ modifications; azido-PEG$_4$ modifications; fluorophore-PEG$_4$ modifications, DyLight 550-PEG$_4$-alkane-3',5'-cytidine-bisphosphate (Dy550P$_4$A-3',5'-pCp, compound 14).

Biotin-PEG$_4$ Modification

One embodiment is a method of preparing biotin-polyethylene glycol (PEG)-alkane-3',5'-cytidine-bisphosphate. The method reacts propargyl amine with methyl trifluoroacetate to result in propargyltrifluoroacetamide. The propargyltrifluoroacetamide reacts with 5-iodocytidine to result in 5-[3-(trifluoroacetamido)propynyl]cytidine. The 5-[3-(trifluoroacetamido)propynyl]cytidine then is converted to 5-[3-(trifluoroacetamido)propyl]cytidine. The 5-[3-(trifluoroacetamido)propyl]cytidine then is converted to 5-(3-aminopropyl)cytidine. The 5-(3-aminopropyl)cytidine then is reacted with NHS-PEG-biotin to result in biotin-PEG-alkane-cytidine. The biotin-PEG-alkane-cytidine then is reacted with diphosphoryl chloride to result in biotin-polyethylene glycol (PEG)-alkane-3',5'-cytidine-bisphosphate.

Proparglytrifluoroacetamide (1) was prepared according to the following reaction:

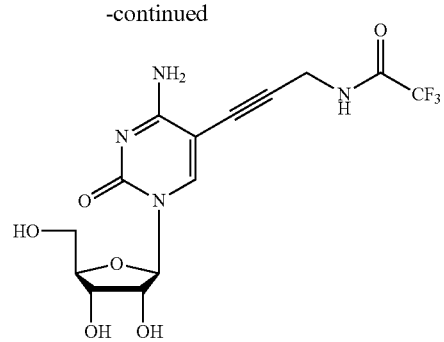

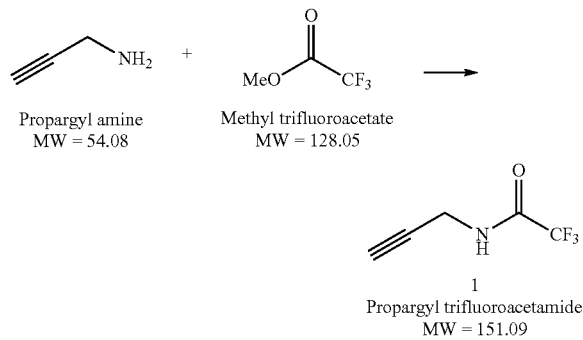

Propargyl amine (4.00 g, 72.62 mmol, 1.00 equiv.) was added dropwise to methyl trifluoroacetate (11.16 g, 87.15 mmol, 1.20 equiv.) at 0° C. The reaction mixture was stirred at 0° C. for 2 h and then concentrated under reduced pressure to remove methanol. The product was purified by vacuum distillation yielding propargyltrifluoroacetamide as a colorless liquid (9.59 g, 87%). The structure was confirmed by $^1$H- and $^{19}$F-NMR.

5-[3-(trifluoroacetamido)propynyl]cytidine (2) was prepared according to the following reaction:

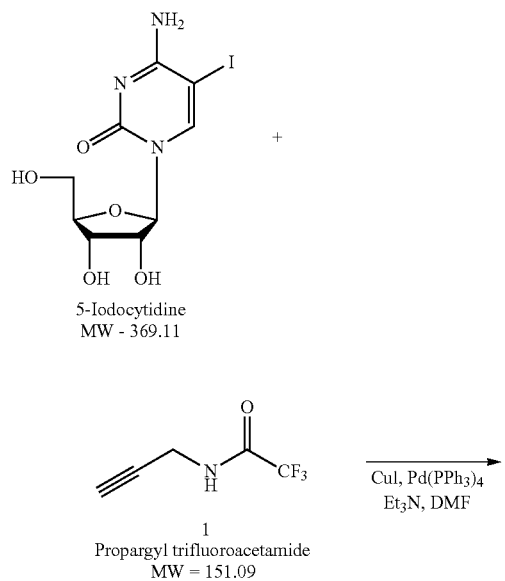

A 100-mL three-necked flask was charged with 5-iodocytidine (2.66 g, 7.00 mmol, 1.00 equiv.), cuprous iodide (0.267 g, 1.40 mmol, 0.20 equiv.) and dry DMF (35 mL). After complete dissolution of the reaction mixture, propargyltrifluoroacetamide (3.17 g, 21.00 mmol, 3.00 equiv.), triethylamine (1.42 g, 14.00 mmol, 2.00 equiv.) and finally tetrakis(triphenylphosphine)palladium(0) (0.809 g, 0.70 mmol, 0.10 equiv.) were added to the reaction mixture under $N_2$. The reaction was stirred at ambient temperature (around 19° C. to around 22° C.) under $N_2$ for 18-24 h. The reaction was then diluted with 70 mL of 1:1 methanol-dichloromethane and the bicarbonate form of AGI X8 resin (12.00 g) was added. After stirring for about one h, the reaction mixture was filtered and the resin was washed with 1:1 methanol-dichloromethane. The combined filtrates were rapidly concentrated with a rotary evaporator. The residue was immediately purified by flash chromatography. Removal of solvent from the appropriate fractions afforded 1.84 g (67%) of 5-[3-(trifluoroacetamido)propynyl]cytidine as a light brown solid, which was confirmed by $^1$H-NMR.

5-[3-(trifluoroacetamido)propyl]cytidine (3) was prepared according to the following reaction:

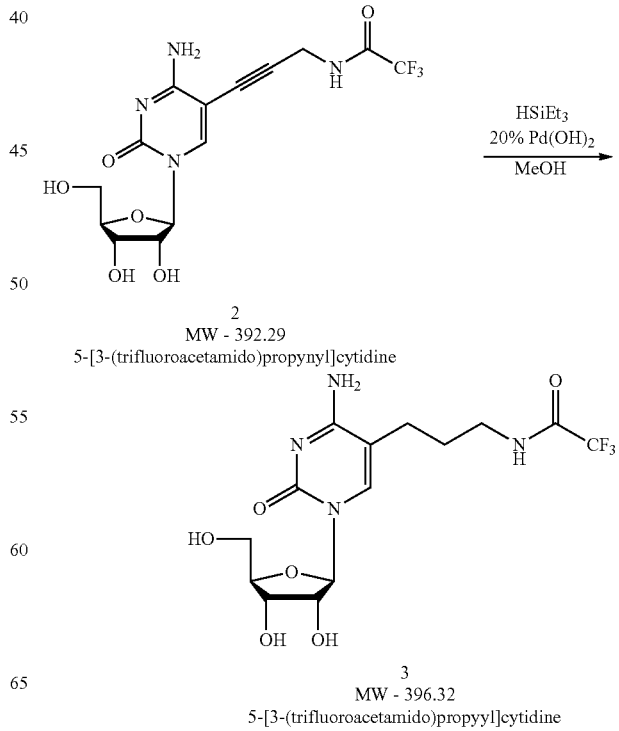

5-[3-(trifluoroacetamido)propynyl]cytidine (1.25 g, 3.19 mmol, 1.00 equiv.) was dissolved in methanol (30 mL). Palladium hydroxide (0.25 g, 20 wt./wt. % based on propynyl cytidine) and triethylsilane (3.71 g, 31.90 mmol, 10.00 equiv.) were added to the reaction mixture. After 20-24 hours at ambient temperature, the reaction mixture was filtered through glass fiber and the filtrate was concentrated under reduced pressure giving a dark brown residue. The residue was purified by flash chromatography. Removal of solvent from the appropriate fractions afforded 0.85 g (71%) of 5-[3-(trifluoroacetamido)propyl]cytidine as a cream colored solid, which was confirmed by $^1$H-NM.

5-(3-aminopropyl)cytidine (4) was prepared according to the following reaction:

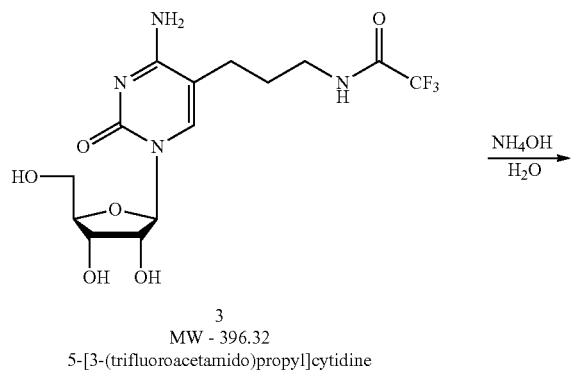

3
MW - 396.32
5-[3-(trifluoroacetamido)propyl]cytidine $\xrightarrow[\text{H}_2\text{O}]{\text{NH}_4\text{OH}}$

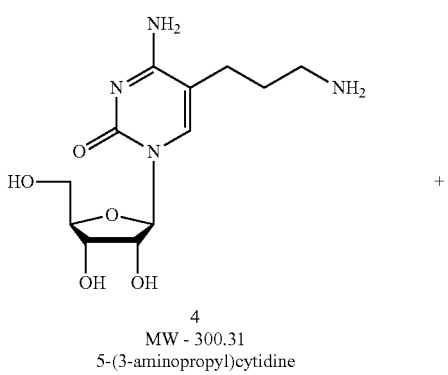

4
MW - 300.31
5-(3-aminopropyl)cytidine

-continued

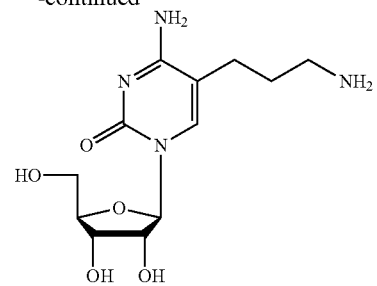

4
MW - 300.31
5-(3-aminopropyl)cytidine

5-[3-(trifluoroacetamido)propyl]cytidine (0.69 g, 1.74 mmol) was dissolved in DI H$_2$O (8.5 mL). After complete dissolution, concentrated ammonium hydroxide (NH$_4$OH) (8.5 mL) was added to the reaction mixture. The reaction solution was stirred at ambient temperature for 2-3 h and then concentrated under reduced pressure giving the crude product as yellow-orange residue. The crude product was dissolved in deionized H$_2$O (10 mL) and AG50W-X8 resin (2.5 g) was added to the solution. The suspension was stirred for 15 min and filtered over a bed of AG50W-X8 resin (2.5 g). The resin was washed with DI H$_2$O and the product was then eluted off of the resin by washing the resin with deionized H$_2$O/conc. NH$_4$OH, 4:1, collecting fractions (monitored by TLC). Removal of solvent from the appropriate fractions afforded 0.51 g (98%) of 5-(3-aminopropyl)cytidine as light tan solid, which was confirmed by $^1$H-NMR.

Biotin-PEG$_4$-alkane-cytidine (BPAC, 5) was prepared according to the following reaction:

+

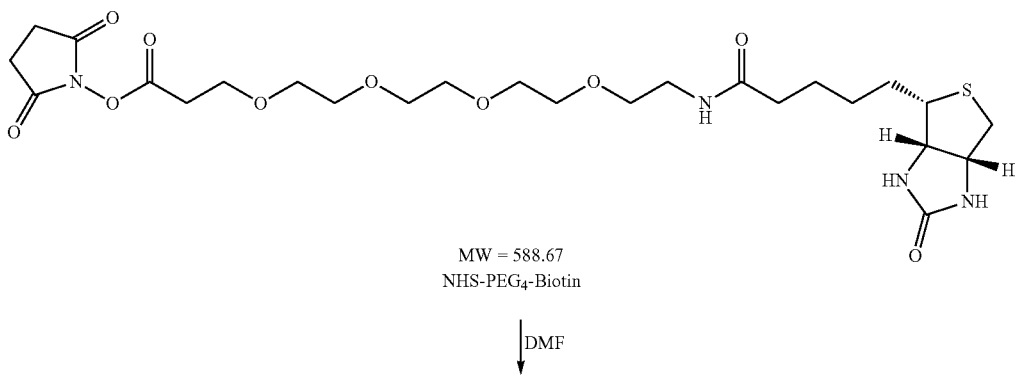

MW = 588.67
NHS-PEG$_4$-Biotin

↓ DMF

-continued

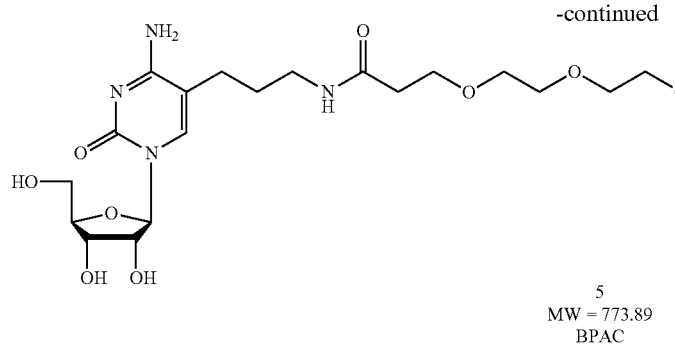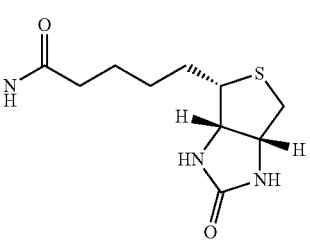

5
MW = 773.89
BPAC

NHS-PEG$_4$-biotin (0.196 g, 0.333 mmol, 1.00 equiv.) was dissolved in DMF (10 mL). 5-(3-aminopropyl)cytidine) (0.100 g, 0.333 mmol, 1.00 equiv.) was added to the reaction solution. The reaction solution was stirred at ambient temperature under N$_2$ atmosphere. After 20-24 h, the reaction mixture was concentrated under reduced pressure giving the crude product. The crude product was purified by flash chromatography. Removal of solvent from the appropriate fractions afforded 0.18 g (69%) of BPAC as a white solid, which was confirmed by $^1$H-NMR.

Biotin-PEG$_4$-alkane-3',5'-cytidine-bisphosphate (BPA-3', 5'-pCp, 6) was prepared according to the following reaction:

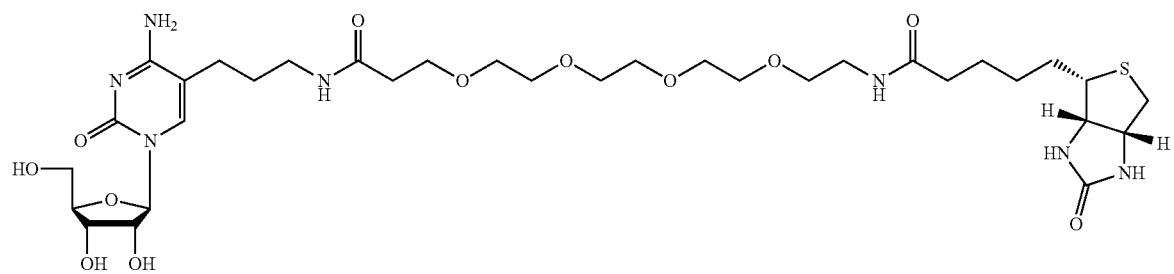

5
MW = 773.89
BPAC

1. Diphosphoryl chloride (structure shown)
2. 0.5M TEAB buffer, pH 8.5
3. C18, FPLC, C18

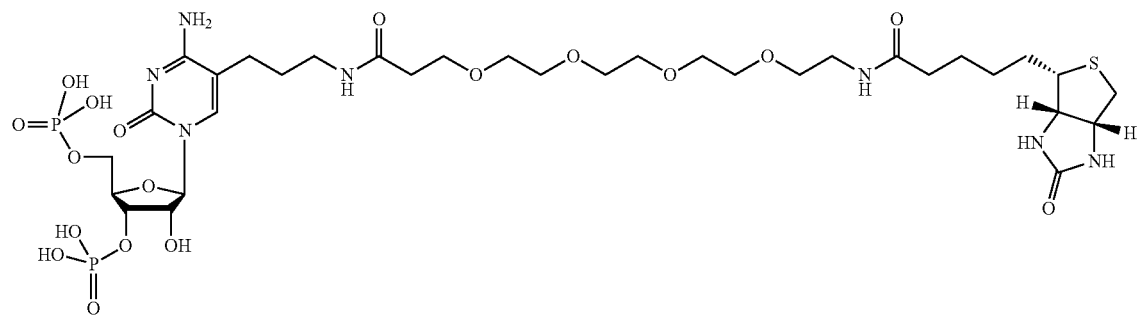

6
MW = 933.85
BPA-3', 5'-pCp

BPAC (0.061 g, 0.079 mmol, 1.00 equiv.) was partially dissolved in diphosphoryl chloride (196 μL, 1.66 mmol, 21.00 equiv.), previously cooled to −10° C. to −15° C. in a 1-mL Reacti-Vial™. The mixture was then stirred at −10° C. to −15° C. After 5 h, the reaction was quenched by addition of ice cold water (1-2 mL) and, immediately thereafter, with a chilled solution of 0.5 M TEAB buffer, pH 8.5 (17 mL). Upon stabilization at neutral pH, the colorless solution was stirred at ambient temperature for 30 min and concentrated using a rotary evaporator until complete removal of TEAB. The solution was desalted using a C18 cartridge (Waters) and purified by FPLC (MonoQ 10/100GL column, GE) using a pH gradient. After a final desalting using again a C18 cartridge (Waters), BPA-3',5'-pCp was isolated after lyophilization as a white solid (10 mg, 9%), which was confirmed by $^1$H-NMR & HPLC.

Overview of Preparation of Biotin-PEG$_4$-SS-Alkane-3',5'-Cytidine-Bisphosphate (BP$_4$SSA-3',5'-pCp, Compound 12)

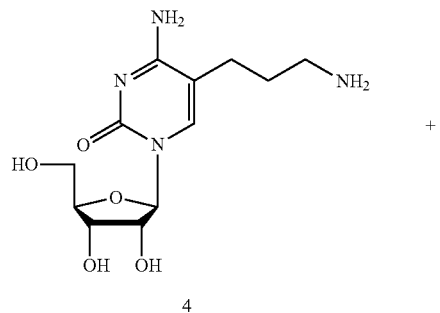

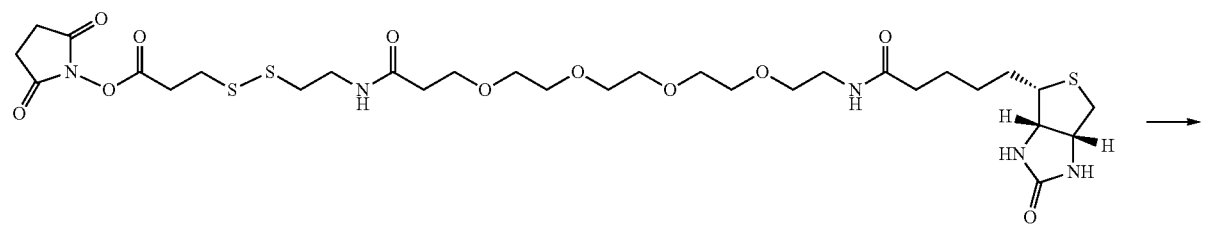

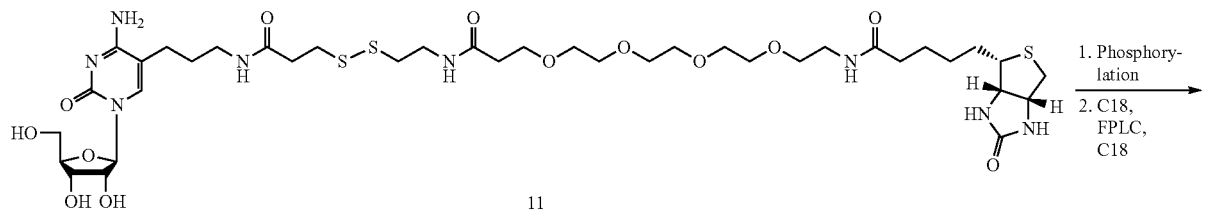

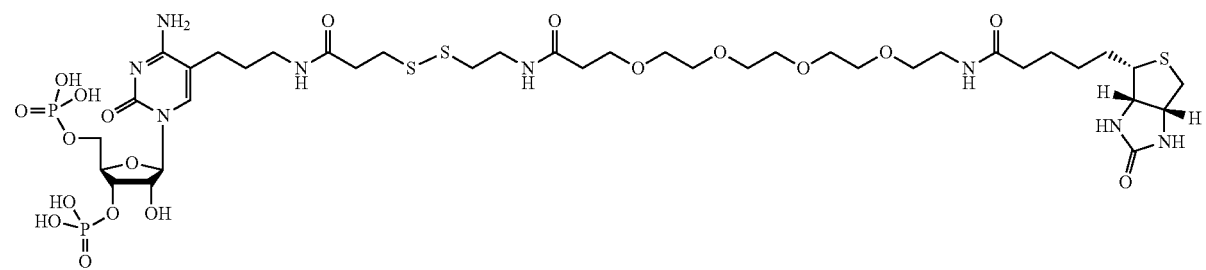

The reaction scheme to prepare biotin-polyethylene glycol (PEG)-SS-alkane-3',5'-cytidine-bisphosphate is as follows. The 5-(3-aminopropyl)cytidine (compound 4) is reacted with NHS-SS-PEG-biotin to result in biotin-PEG-SS-alkane-cytidine (compound 11). The biotin-PEG-SS-alkane-cytidine (compound 11) then is reacted with diphosphoryl chloride to result in biotin-polyethylene glycol (PEG)-SS-alkane-3',5'-cytidine-bisphosphate (compound 12).

Preparation of Biotin-PEG$_4$-SS-Alkane-Cytidine (BP$_4$SSAC, Compound 11)

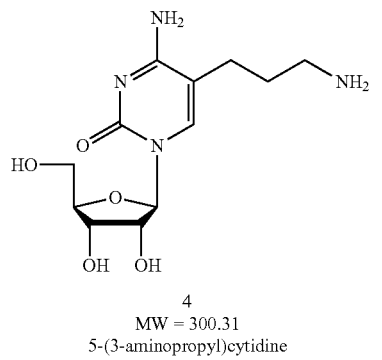

4
MW = 300.31
5-(3-aminopropyl)cytidine

+

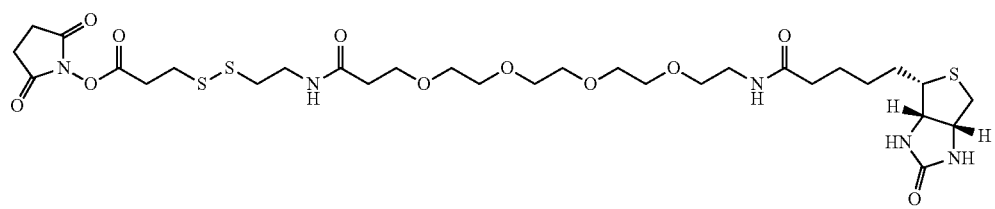

MW = 751.93
NHS-SS-PEG$_4$-Biotin

↓ DMF

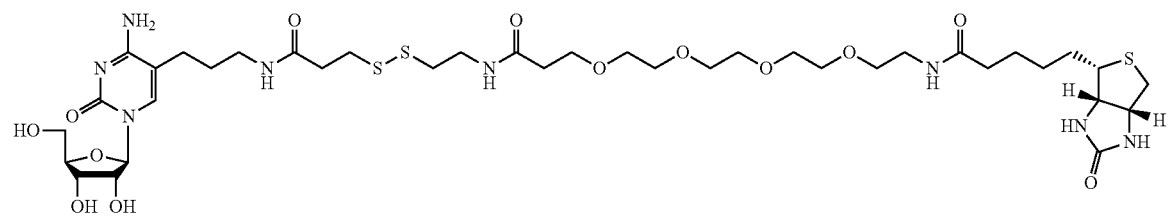

11
MW = 937.16
Biotin-PEG$_4$-SS-Alkane-Cytidine
(BP$_4$SSAC)

NHS-SS-PEG₄-biotin (0.250 g, 0.333 mmol, 1.00 equiv.) was dissolved in DMF (10 mL). 5-(3-aminopropyl)cytidine) (0.100 g, 0.333 mmol, 1.00 equiv.) was added to the reaction solution. The reaction solution was stirred at ambient temperature under N₂ atmosphere. After 20-24 hours, the reaction mixture was concentrated under reduced pressure giving the crude product. The crude product was purified by flash chromatography. Removal of solvent from the appropriate fractions afforded 0.19 g (61%) of BP₄SSAC (compound 11) as a white solid, which was confirmed by ¹H-NMR.

Preparation of Biotin-PEG₄-SS-Alkane-3',5'-Cytidine-Bisphosphate (BP₄SSA-3',5'-pCp, Compound 12)

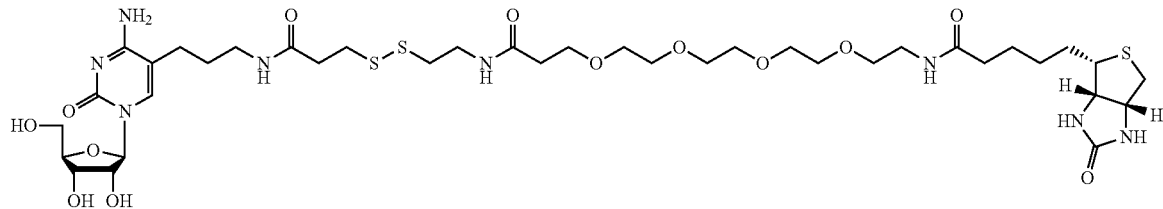

11
MW = 937.16
Biotin-PEG₄-SS-Alkane-Cytidine
(BP₄SSAC)

1.

Diphosphoryl chloride 2. 0.5M TEAB buffer, pH 8.5
3. C18, FPLC, C18

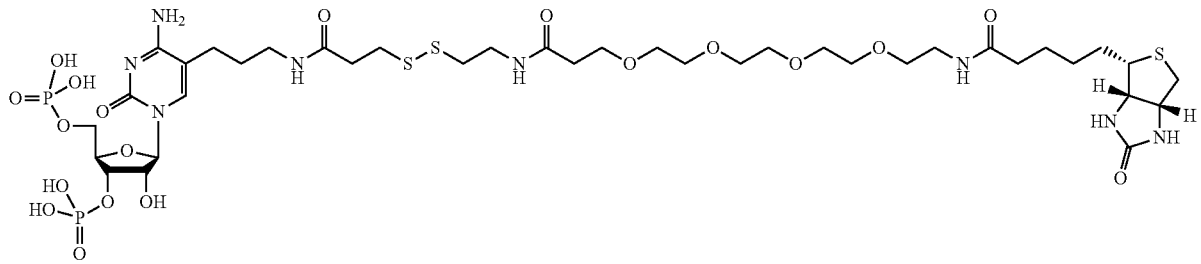

12
MW = 1097.12
Biotin-PEG₄SS-Alkane-3',5'-Bisphosphate-Cytidine

BP₄SSAC (0.074 g, 0.079 mmol, 1.00 equiv.) was partially dissolved in diphosphoryl chloride (196 μL, 1.66 mmol, 21.00 equiv.), previously cooled to −10° C. to −15° C. in a 1-mL Reacti-Vial™. The mixture was then stirred at −10° C. to −15° C. After five hours, the reaction was quenched by addition of ice cold water (1-2 mL) and, immediately thereafter, with a chilled solution of 0.5M TEAB buffer, pH 8.5 (17 mL). Upon stabilization at neutral pH, the colorless solution was stirred at ambient temperature for 30 min and concentrated using a rotary evaporator until complete removal of TEAB. The solution was desalted using a C18 cartridge (Waters) and purified by FPLC (MonoQ 10/100GL column, GE) using a pH gradient. After a final desalting using again a C18 cartridge (Waters), BP₄SSA-3',5'-pCp (compound 12) was isolated after lyophilization as a white solid (5 mg, 6%), which was confirmed by ¹H-NMR and HPLC.

Biotin-PEG$_{12}$ Modification

Preparation of Biotin-PEG$_{12}$-Alkane-Cytidine (BP$_{12}$AC, Compound 7)

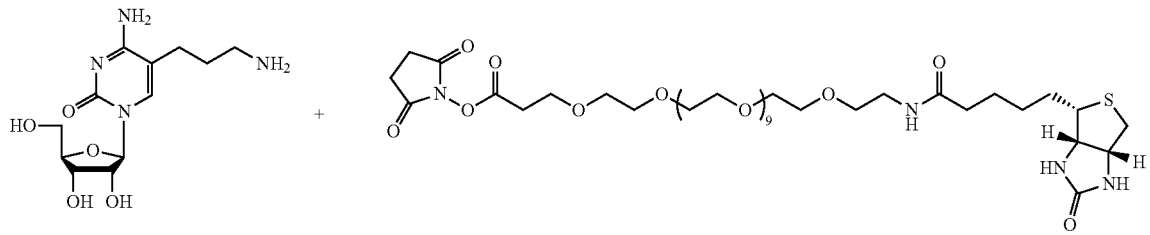

4
MW = 300.31
5-(3-aminopropyl)cytidine

MW = 941.09
NHS-PEG$_{12}$-Biotin

↓ DMF

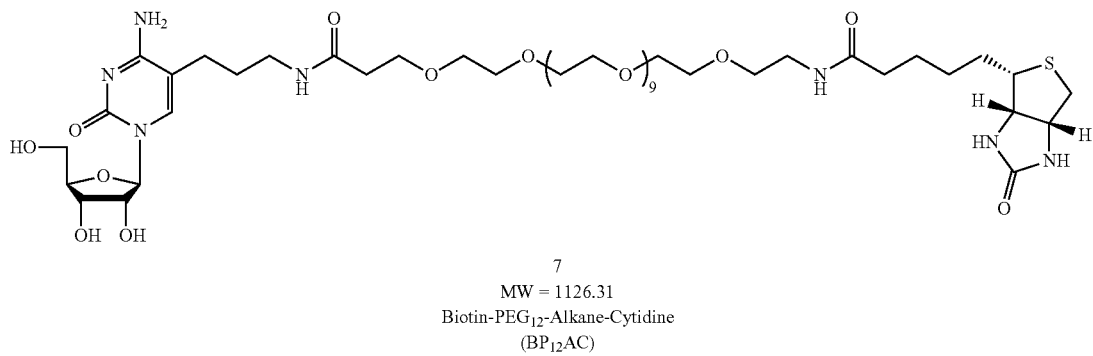

7
MW = 1126.31
Biotin-PEG$_{12}$-Alkane-Cytidine
(BP$_{12}$AC)

NHS-PEG$_{12}$-biotin (0.313 g, 0.333 mmol, 1.00 equiv.) was dissolved in DMF (10 mL). 5-(3-aminopropyl)cytidine) (0.100 g, 0.333 mmol, 1.00 equiv., compound 4) was added to the reaction solution. The reaction solution was stirred at ambient temperature under N$_2$ atmosphere. After 20-24 h, the reaction mixture was concentrated under reduced pressure giving the crude product. The crude product was purified by flash chromatography. Removal of solvent from the appropriate fractions afforded 0.27 g (72%) of BP$_{12}$AC (compound 7) as a light yellow foam, which was confirmed by $^1$H-NMR.

Preparation of Biotin-PEG$_{12}$-Alkane-3',5'-Bisphosphate-Cytidine (BP$_{12}$A-3',5'-pCp, Compound 8)

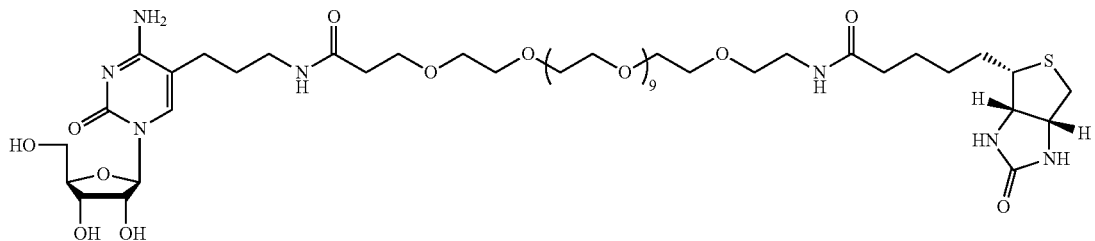

7
MW = 1126.31
Biotin-PEG$_{12}$-Alkane-Cytidine
(BP$_{12}$AC)

1.

Diphosphoryl chloride 2. 0.5M TEAB buffer, pH 8.5
3. C18, FPLC, C18

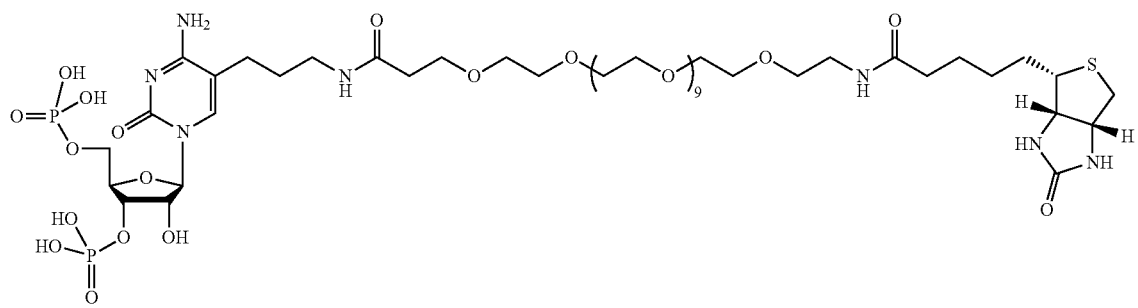

8
MW = 1286.27
Biotin-PEG$_{12}$-Alkane-3',5'-Bisphosphate-Cytidine
(BP$_{12}$A-3',5'-pCp)

Biotin-PEG$_{12}$-alkane-cytidine (0.135 g, 0.120 mmol, 1.00 equiv., compound 7) was partially dissolved in diphosphoryl chloride (315 µL, 2.40 mmol, 20.00 equiv.), previously cooled to −10 to −15° C. in a 1-mL Reacti-Vial™. The mixture was stirred at −10 to −15° C. After five hours, the reaction was quenched by adding ice cold water (1-2 mL) and immediately after with a chilled solution of 0.5M TEAB buffer, pH 8.5 (40 mL). Upon stabilization at neutral pH, the colorless solution was stirred at ambient temperature for 30 min and concentrated using a rotary evaporator until TEAB was completely removed. The solution was desalted using a C18 cartridge (Waters) and purified by FPLC (MonoQ 10/100GL column, GE) using a pH gradient. After final desalting using a C18 cartridge (Waters), biotin-PEG$_{12}$-alkane-3',5'-cytidine-bisphosphate (compound 8) was isolated after lyophilization as a sticky white solid (8 mg, 5%), which was confirmed by 1H-NMR and HPLC.

Azido-PEG$_4$ Modification

Azido-PEG$_4$-alkane-3',5'-cytidine-bisphosphate, Compound 9

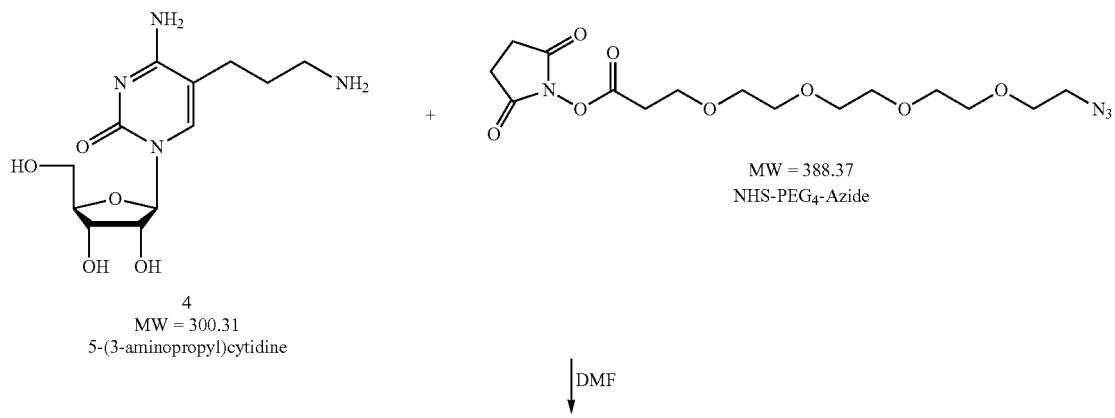

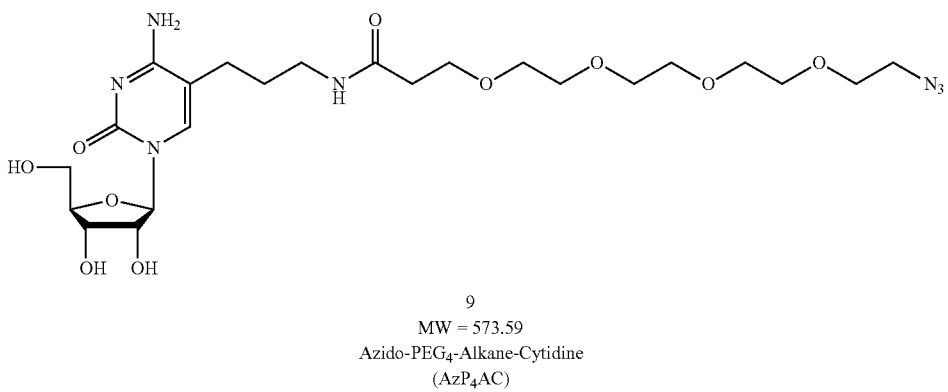

One embodiment is a method of preparing azido-PEG$_4$-alkane-3',5'-cytidine-bisphosphate. The 5-(3-aminopropyl)cytidine was synthesized as described above, then was reacted with NHS-PEG$_4$-azide to result in azido-PEG$_4$-alkane-cytidine. The azido-PEG$_4$-alkane-cytidine was then reacted with diphosphoryl chloride to result in azido-PEG$_4$-alkane-3',5'-cytidine-bisphosphate.

NHS-PEG$_4$-azide (0.408 g, 1.05 mmol, 1.00 equiv.) was dissolved in DMF (32 mL). The 5-(3-aminopropyl)cytidine) (0.315 g, 1.05 mmol, 1.00 equiv.) was added to the reaction solution. The reaction solution was stirred at ambient temperature under N$_2$ atmosphere. After 20-24 hours, the reaction mixture was concentrated under reduced pressure giving the crude product. The crude product was purified by flash chromatography. Removal of solvent from the appropriate fractions afforded 0.378 g (63%) of azido-PEG$_4$-alkane-cytidine (compound 9) as a near colorless glass, which was confirmed by 1H-NMR.

Azido-PEG$_4$-alkane-3',5'-Bisphosphate-Cytidine (AzP$_4$A-3',5' p-C-p), Compound 10

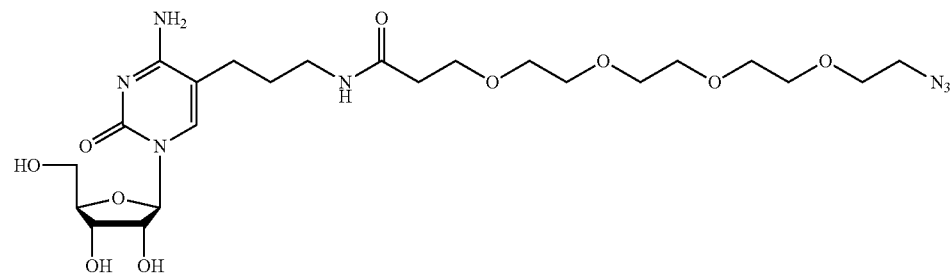

9
MW = 573.59
Azido-PEG$_4$-Alkane-Cytidine
(AzP$_4$AC)

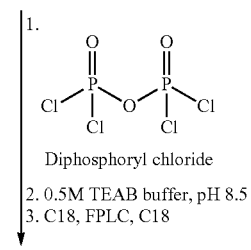

1.

Diphosphoryl chloride 2. 0.5M TEAB buffer, pH 8.5
3. C18, FPLC, C18

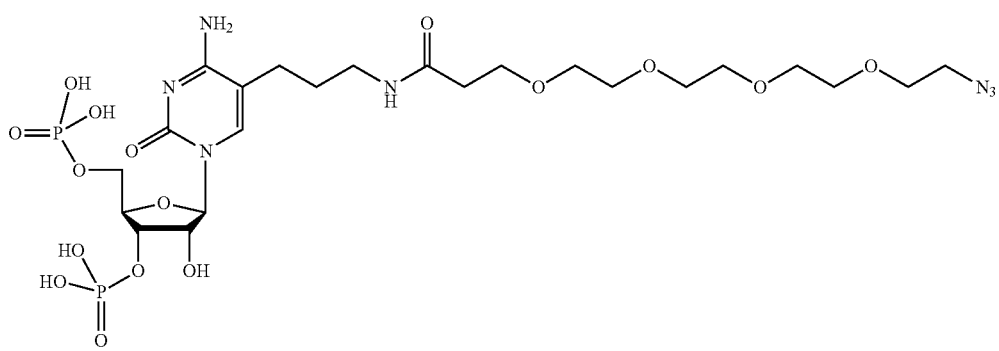

10
MW = 733.55
Azido-PEG$_4$-Alkane-3',5'-Bisphosphate-Cytidine
(AzP$_4$A-3',5'-pCp)

Azido-PEG$_4$-alkane-cytidine (0.150 g, 0.262 mmol, 1.00 equiv., compound 9) was partially dissolved in diphosphoryl chloride (688 µL, 5.24 mmol, 20.00 equiv.), previously cooled to −10 to −15° C. in a 1 mL Reacti-Vial™. The mixture was then stirred at −10 to −15° C. After five hours, the reaction was quenched by adding ice cold water (2-3 mL) and then immediately with a chilled solution of 0.5M TEAB buffer, pH 8.5 (87 mL). Upon stabilization at neutral pH, the colorless solution was stirred at ambient temperature for 30 min and concentrated using a rotary evaporator until TEAB was complete removed. The solution was desalted using a C18 cartridge (Waters) and purified by FPLC (MonoQ 10/100GL column, GE) using a pH gradient. After final desalting using again a C18 cartridge (Waters), azido-PEG$_4$-alkane-3',5'-cytidine-bisphosphate (compound 10) was isolated after lyophilization as a sticky white solid (10 mg, 6%), confirmed by 1H-NMR and HPLC.

Fluorophore-PEG$_4$ Modifications

Overview—Preparation of DyLight 550-PEG$_4$-Alkane-3',5'-Cytidine-Bisphosphate (Dy550P$_4$A-3',5'-pCp, 14)

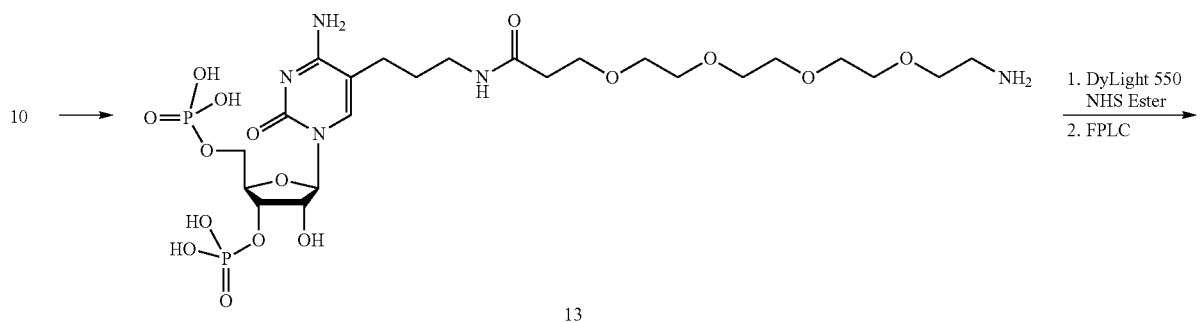

13

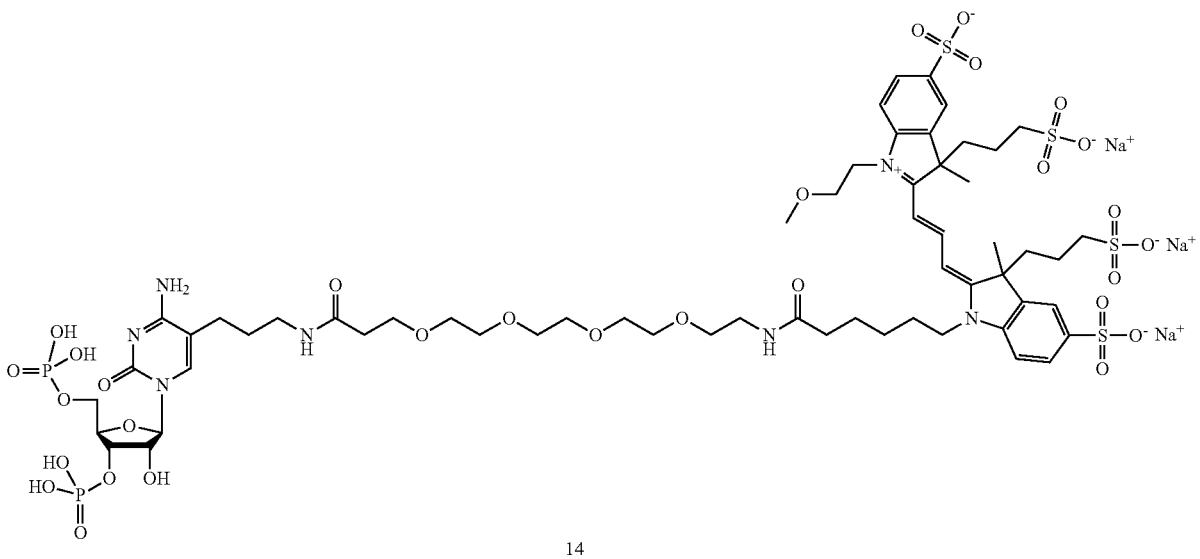

14

DyLight 550-polyethylene glycol (PEG)-alkane-3',5'-cytidine-bisphosphate (compound 14) is prepared as follows. The azido-PEG$_4$-alkane-3',5'-cytidine-bisphosphate (compound 10) was synthesized as described above, then allowed to react with tris(2-carboxyethyl)phosphine hydrochloride (TCEP) to result in amino-PEG$_4$-alkane-3',5'-cytidine bisphosphate (compound 13). The amino-PEG$_4$-alkane-3',5'-cytidine bisphosphate (compound 13) was then reacted with DyLight 550 NHS ester to result in 550-polyethylene glycol (PEG)-alkane-3',5'-cytidine-bisphosphate (compound 14).

Preparation of Amino-PEG$_4$-Alkane-3',5'-Bisphosphate-Cytidine (AmP$_4$A-3',5'-pCp, 13)

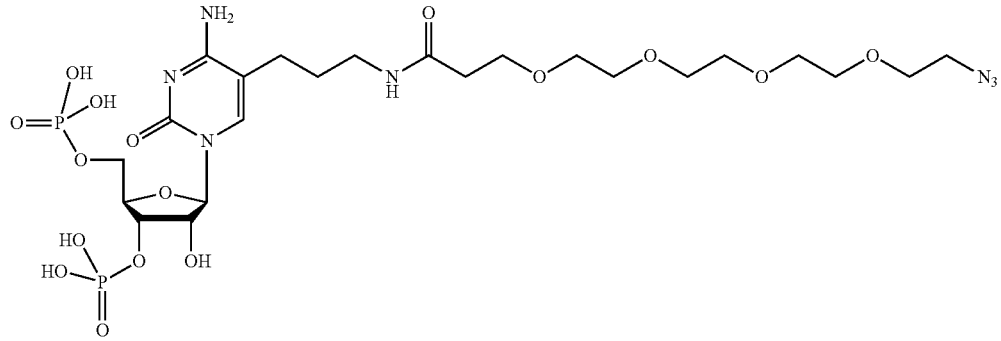

10
MW = 733.55
Azido-PEG$_4$-Alkane-3',5'-Bisphosphate-Cytidine
(AzP$_4$A-3',5'-pCp)

1. TCEP
2. FPLC

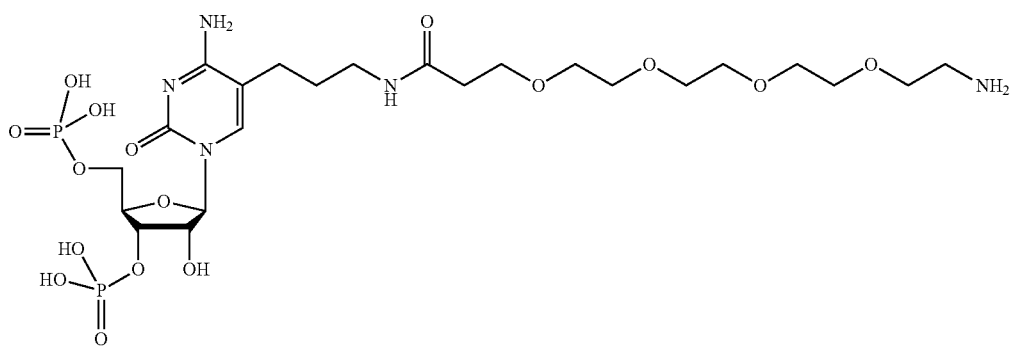

13
MW = 707.56
Amino-PEG$_4$-Alkane-3',5'-Bisphosphate-Cytidine
(AmP$_4$A-3',5'-pCp)

Azido-PEG₄-alkane-3',5'-bisphosphate-cytidine (3.56 μmol, 1.00 equiv., compound 10) was dissolved in 200 mM Tris/HCl, pH 7.5 (800 μL). Tris(2-carboxyethyl)phosphine hydrochloride (TCEP) (17.54 mg, approx. 5.00 equiv.) was dissolved in 200 mM Tris/HCl, pH 7.5 (688 μL). The TCEP solution (200 μL) was added to the solution of azide and the reaction was mixed at ambient temperature. After 1-3 h, the reaction mixture was purified by FPLC and the fractions containing product were treated directly with DyLight 550 NHS ester to result in amino-PEG₄-alkane-3',5'-bisphosphate cytidine (compound 13).

Preparation of DyLight550-PEG₄-Alkane-3',5'-Bisphosphate-Cytidine (Dy550P₄A-3',5'-pCp, 14)

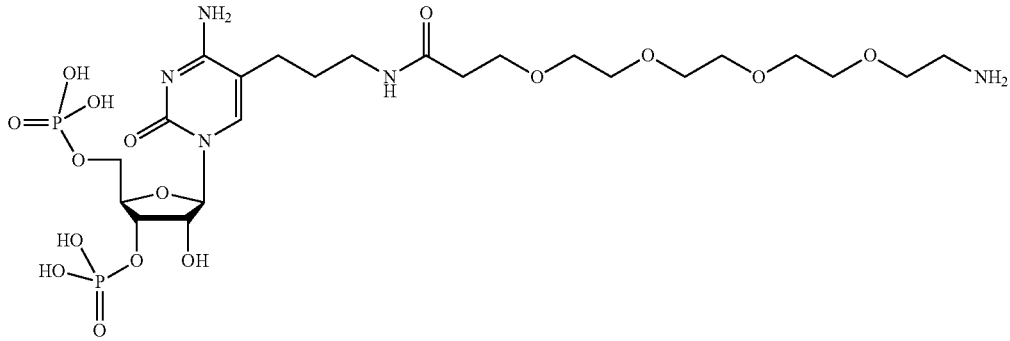

13
MW = 707.56
Amino-PEG₄-Alkane-3',5'-Bisphosphate-Cytidine
(AmP₄A-3', 5'-pCp)

1. DyLight 550 NHS Ester
2. FPLC

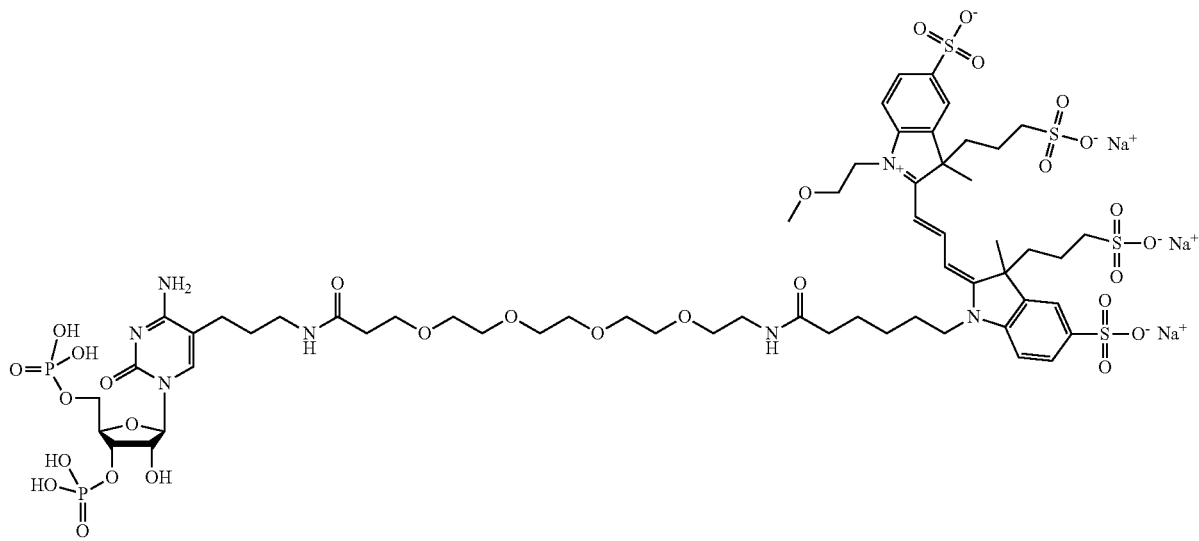

14
MW = 1632.52
DyLight550-PEG₄-Alkane-3',5'-Bisphosphate-Cytidine
(Dy550P₄A-3',5'-pCp)

The pH of an FPLC fraction (2 mL) containing amino-PEG$_4$-alkane-3',5'-bisphosphate-cytidine (compound 13) was adjusted to pH 7.0 by adding 1M HEPES, pH 7.3. Separately, a 1 mM solution of DyLight 550 NHS ester was prepared by dissolving DyLight 550 NHS ester (MW=1040.05, 1 mg) in ultra pure water (960 μL). Amino-PEG$_4$-alkane-3',5'-bisphosphate-cytidine (0.25 mL) and DyLight 550 NHS ester (0.25 mL) were combined in a separate reaction vessel and were mixed with rotation for 1 h at ambient temperature. The reaction mixture was purified by FPLC (MonoQ 10/100GL column, GE) using a pH and salt gradient. Fractions containing product were dialyzed and subsequently lyophilized, yielding DyLight550-PEG$_4$-alkane-3',5'-cytidine-bisphosphate (compound 14) as a dark pink residue.

Other exemplary compounds follow. Examples of fluorescent compounds include, but are not limited to, the following:

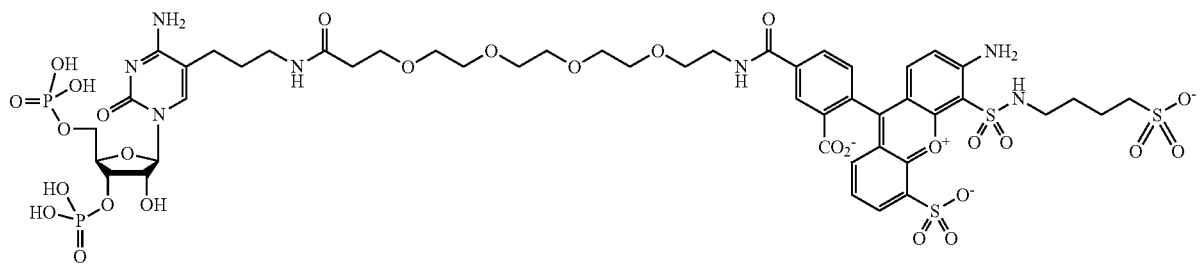

DryLight488-PEG$_4$-Alkane-3',5'-Bisphosphate-Cytidine
(Dy488P$_4$A-3',5'-pCp)

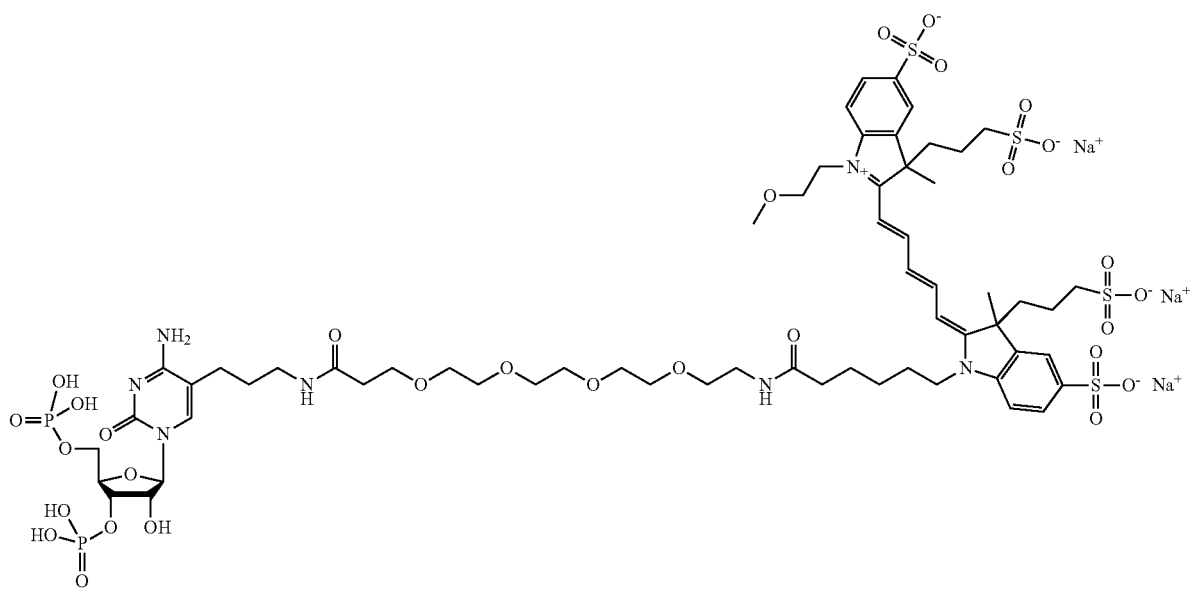

DryLight650-PEG$_4$-Alkane-3',5'-Bisphosphate-Cytidine
(Dy650P$_4$A-3',5'-pCp)

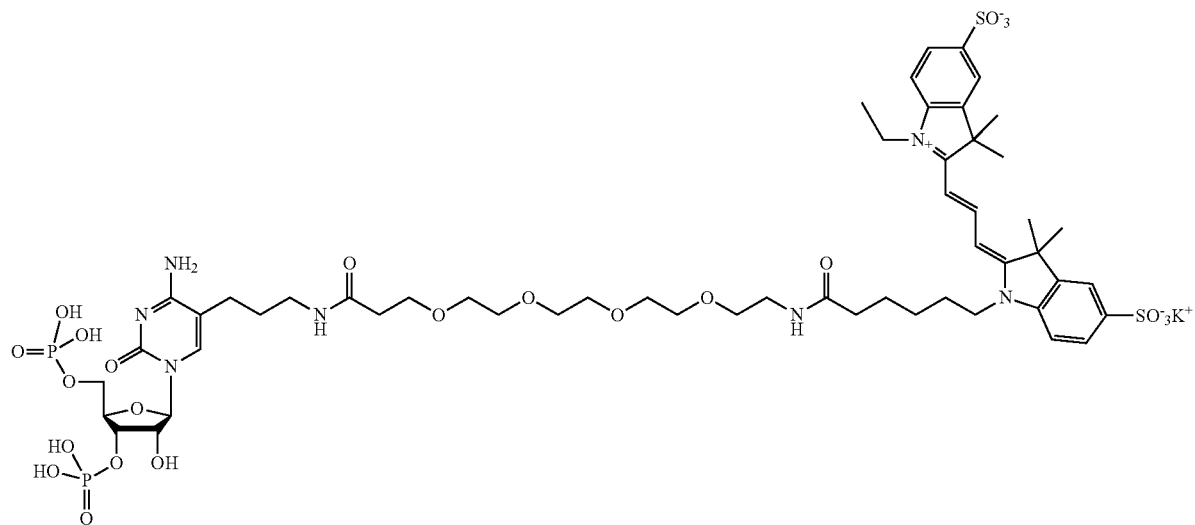
Cy3-PEG₄-Alkane-3′,5′-Bisphosphate-Cytidine
(Cy3P₄A-3′,5′-pCp)
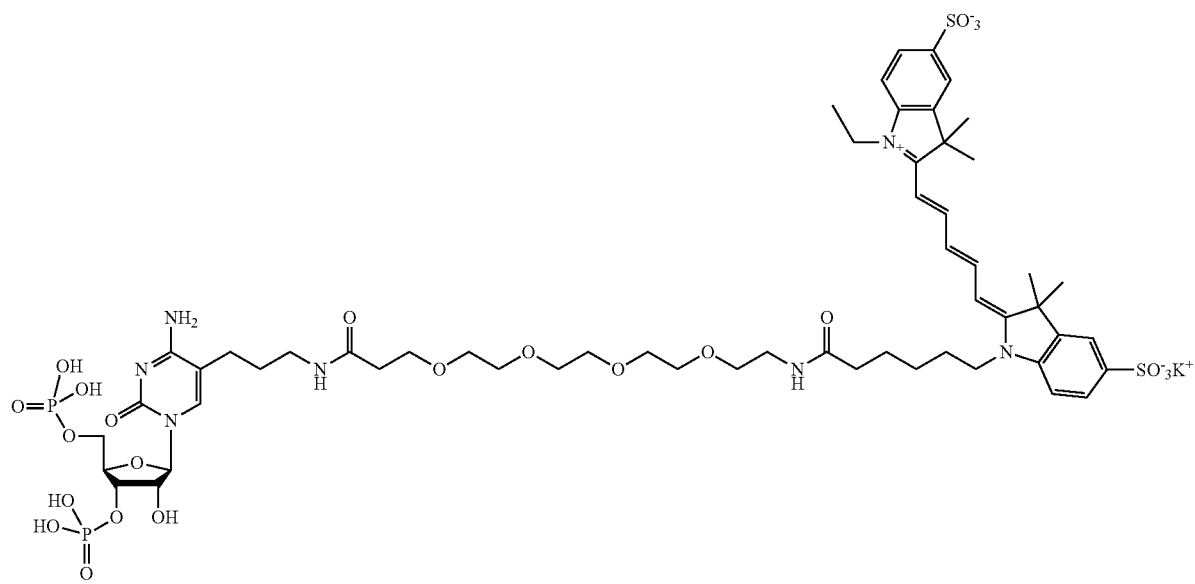
Cy5-PEG₄-Alkane-3′,5′-Bisphosphate-Cytidine
(Cy5P₄A-3′,5′-pCp)
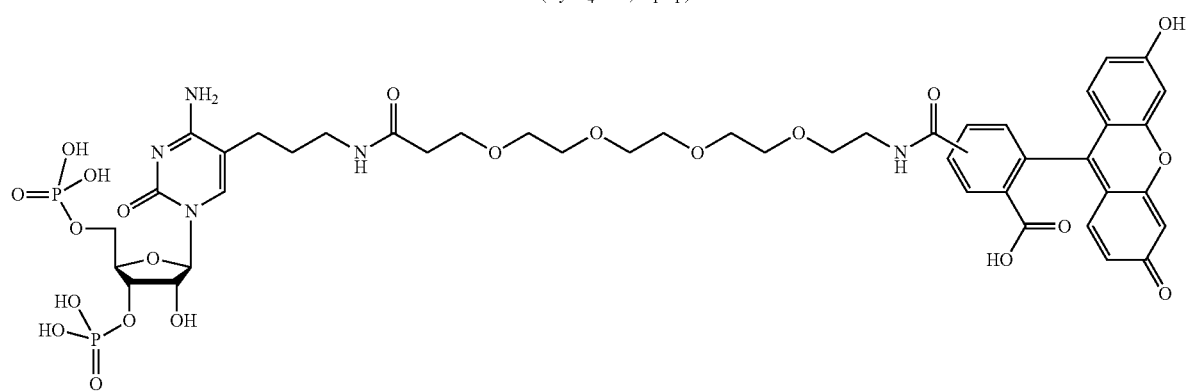
5/6-Carboxyfluorescein-PEG₄-Alkane-3′,5′-Bisphosphate-Cytidine
(5/6-FP₄A-3′,5′-pCp)

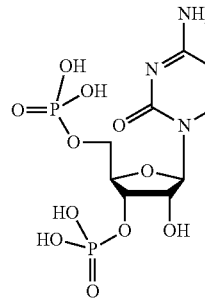
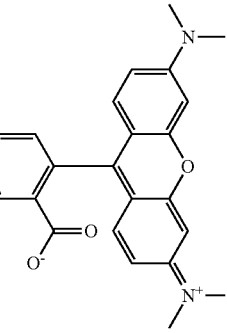
5/6-Carboxytetramethylrhodamine-PEG₄-Alkane-3′,5′-Bisphosphate-Cytidine
(5/6-RP₄A-3′,5′-pCp)
Examples of compounds with mass labels include, but are not limited to, the following:
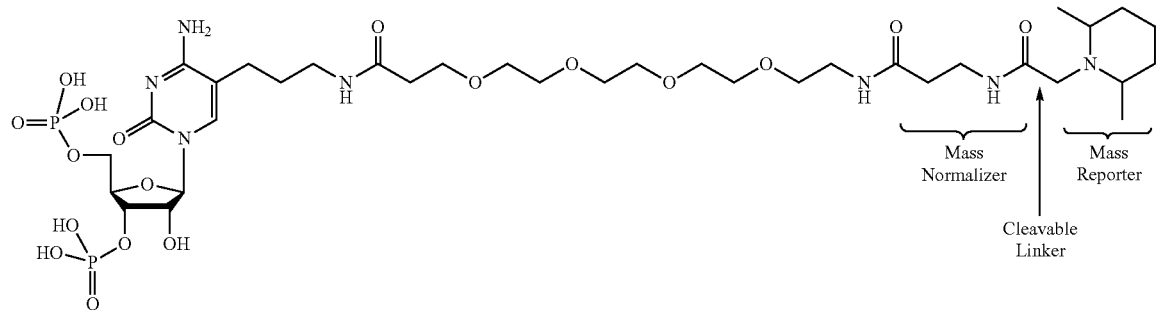
TMT-PEG₄-Alkane-3′,5′-Bisphosphate-Cytidine
(TMTP₄A-3′,5′-pCp)
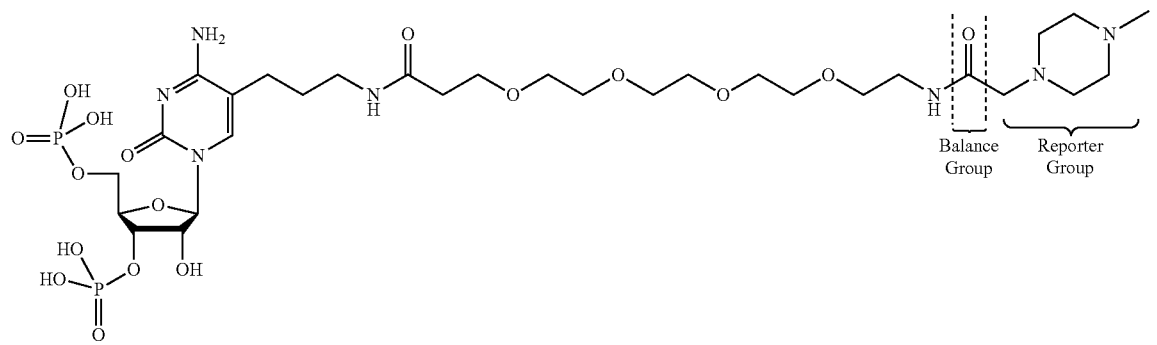
iTRAQ-PEG₄-Alkane-3′,5′-Bisphosphate-Cytidine
(iTRAQP₄A-3′,5′-pCp)

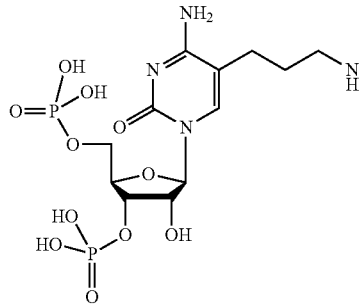
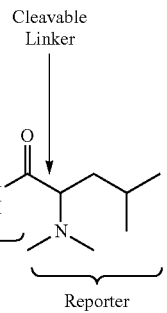
DiART-PEG₄-Alkane-3′,5′-Bisphosphate-Cytidine
(DiARTP₄A-3′,5′-pCp)
Examples of compounds with a spin label include, but are not limited to, the following:
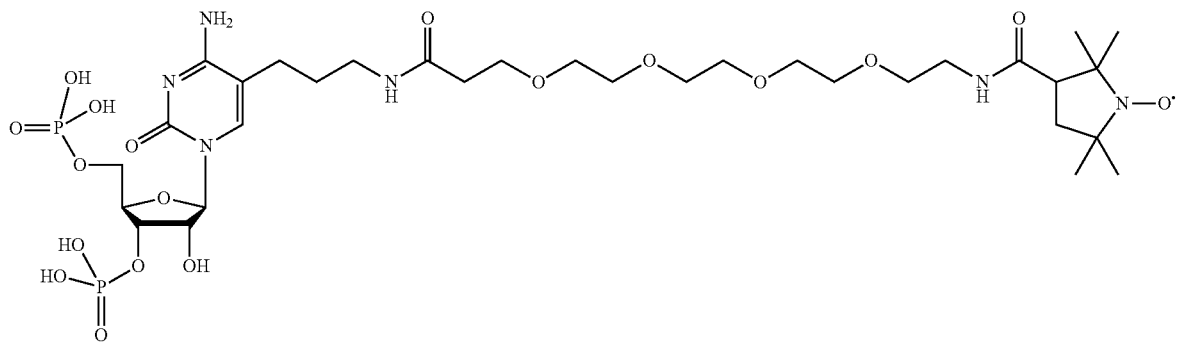
Proxyl-PEG₄-Alkane-3′,5′-Bisphosphate-Cytidine
(PP₄A-3′,5′-pCp)
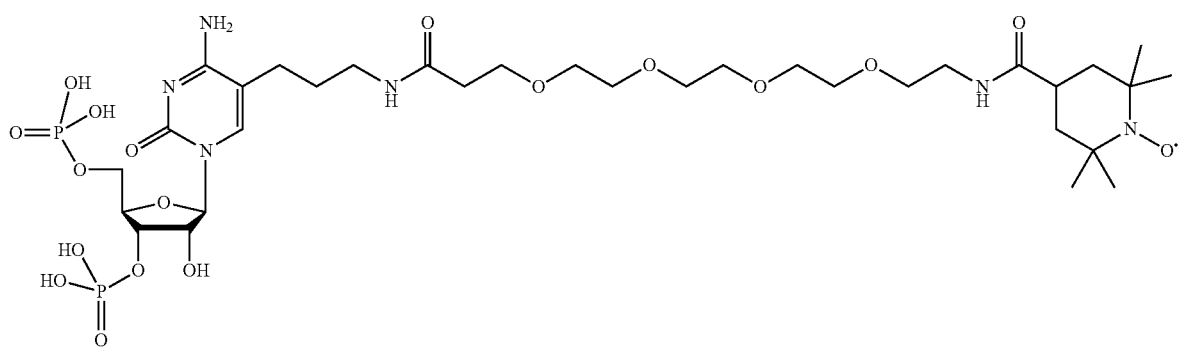
TEMPO-PEG₄-Alkane-3′,5′-Bisphosphate-Cytidine
(TP₄A-3′,5′-pCp)

An example of a desthiobiotin-containing compound is:

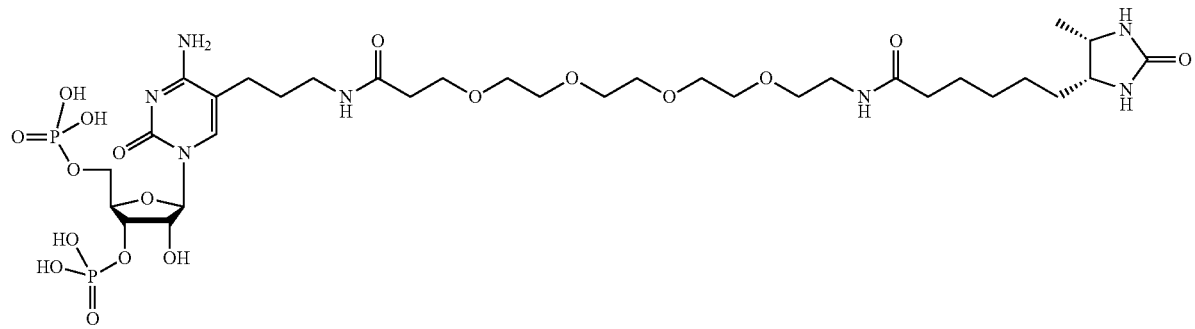

Desthiobiotin-PEG$_4$-Alkane-3′,5′-Bisphosphate-Cytidine
(DP$_4$A-3′,5′-pCp)

Examples of compounds with alternative cleavage include, but are not limited to, the following:

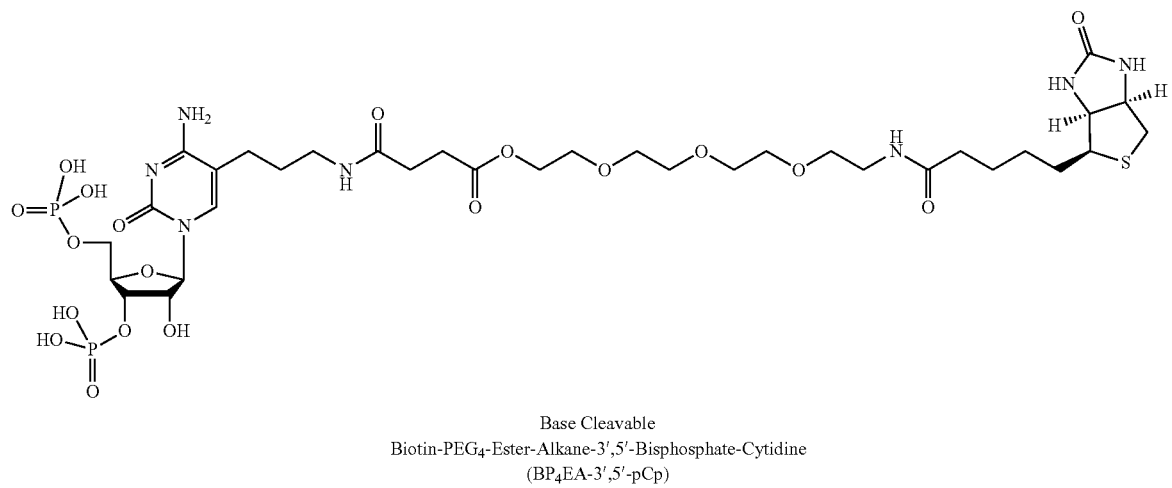

Base Cleavable
Biotin-PEG$_4$-Ester-Alkane-3′,5′-Bisphosphate-Cytidine
(BP$_4$EA-3′,5′-pCp)

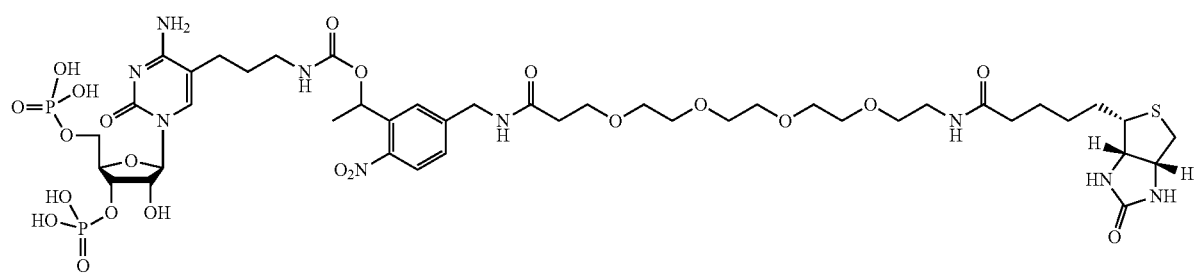

Photocleavable
Biotin-PEG$_4$-Photo-Alkane-3′,5′-Bisphosphate-Cytidine
(BP$_4$PA-3′,5′-pCp)

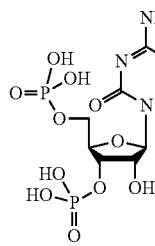

Reduction Cleavable
Biotin-PEG<sub>4</sub>-NN-Alkane-3′,5′-Bisphosphate-Cytidine
(BP<sub>4</sub>NNA-3′,5′-pCp)

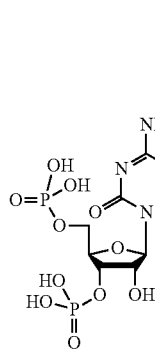

Acid Cleavable
Biotin-PEG<sub>4</sub>-Acid-Alkane-3′,5′-Bisphosphate-Cytidine
(BP<sub>4</sub>AA-3′,5′-pCp)

One embodiment is a kit to label RNA with the compound described above. In one embodiment, the kit contains the compound(s), ligase, ligase buffer, and labeling instructions. In one embodiment, the kit contains additional kit components to enhance ligation efficiency including polyethylene glycol as a size exclusion reagent and DMSO to relax secondary structure. In one embodiment, the kit also includes a control RNA that ligates with greater than 75% efficiency, and a synthetic biotinylated RNA control to assess ligation efficiency. Instructions include methods for a typical ligation reaction using the reagents listed and/or instructions for using a nucleic acid comprising the labeled nucleotide in a method, such as mobility shift, Northern blot, pull-down assay, or in situ hybridization. In one embodiment, the kit contains a described compound where the sugar is ribose, the purine or pyrimidine base is C, m is 3, Lnk is

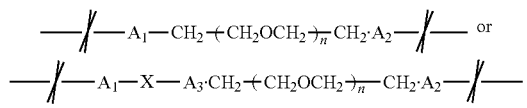

n is 4, $A_1$ is

$A_2$ is

and when present, $A_3$ is

and Obs is selected from the group consisting of biotin, a fluorophore, and an azide.

For mobility shift assays, an excess of the labeled RNA was incubated with a solution containing the protein, RNA, or DNA of interest in an optimized binding buffer. The incubation conditions were empirically determined; incubation time typically ranged from 5 minutes to 1 hour, incubation temperatures typically ranged from 4° C. to room temperature (19° C. to 22° C.). The binding reaction was then subjected to electrophoresis to separate RNA binding complexes from free probe. The shifted RNA complex was then detected in-gel, or transferred to a positively charged membrane and detected using secondary detection reagents (i.e., with a chromogen, or by chemiluminescence).

For Northern blotting, the labeled RNA was used for the detection of RNA that had been separated by electrophoresis and transferred onto a membrane. The labeled RNA was denatured for 5-10 minutes at 95° C. and quickly cooled on ice to less than 10° C. The denatured probe was then added to an optimized hybridization solution and incubated with the membrane at an empirically determined temperature for at least 1 hour, but up to overnight. The membrane was then washed and RNA was detected using secondary detection reagents (i.e., chromogen, by chemiluminescence).

For an assay using a labeled RNA to enrich for a component, whether the substance containing the component was bound to a chip, resin, etc. (e.g., a "pull-down" assay), labeled RNA was incubated in &binding reaction containing the protein, RNA, or DNA of interest, an optimized binding buffer, and affinity resin. The resin was then washed, the RNA complex was eluted, and the protein, DNA, or RNA of interest was detected using techniques including but not limited to PCR, RT-PCR, Western blot, or microarray.

For in situ hybridization, the labeled RNA is used as a probe for the detection of the RNA or RNA complex of interest in cells. The labeled RNA may be used after cells have been fixed onto a support (i.e., a microscope slide, coverslip, tissue dish, microwell, etc.), or in suspension for flow cytometric analysis. Similarly, the labeled RNA may be transfected into live cells, and detected directly or using secondary reagents. The RNA or RNA complex is visualized using techniques including but not limited to light or fluorescent microscopy, flow cytometric analysis, or microarray.

Figure 2:
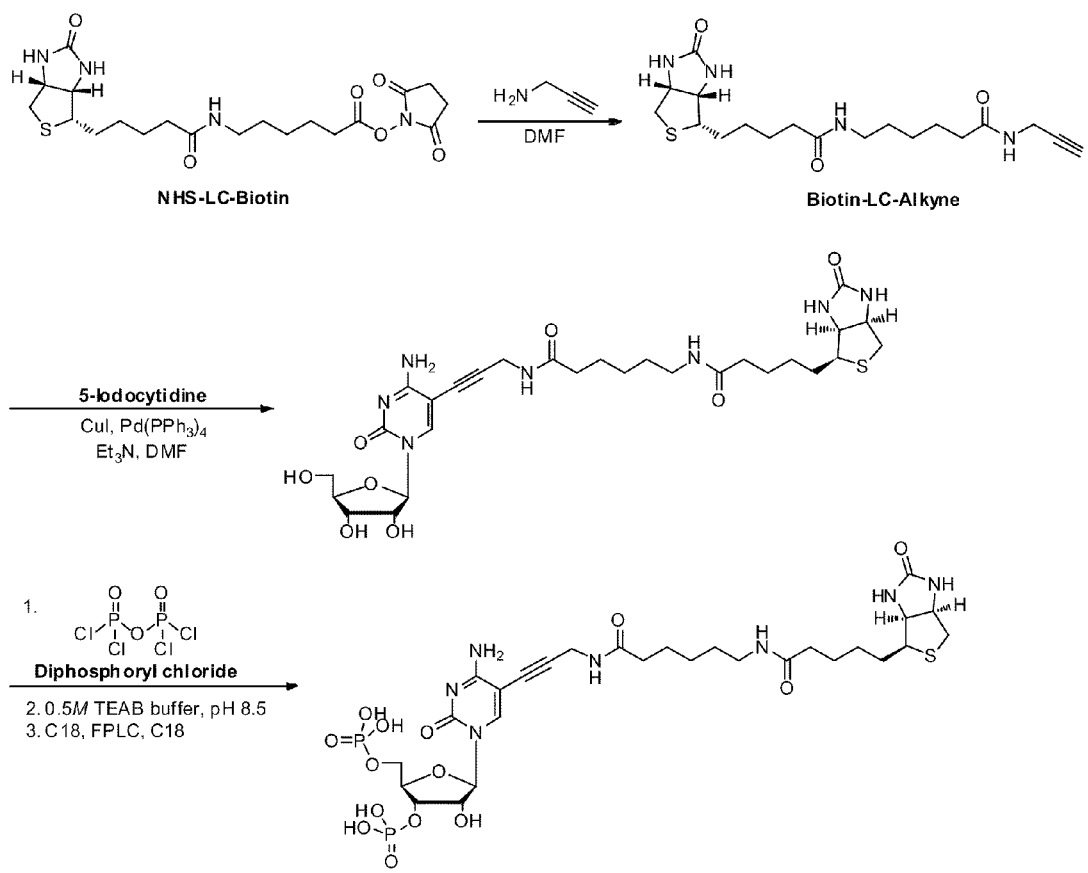
FIG. 2 shows synthesis of biotin-linker-alkyne-3',5' cytidine bisphosphate.
Figure 3:
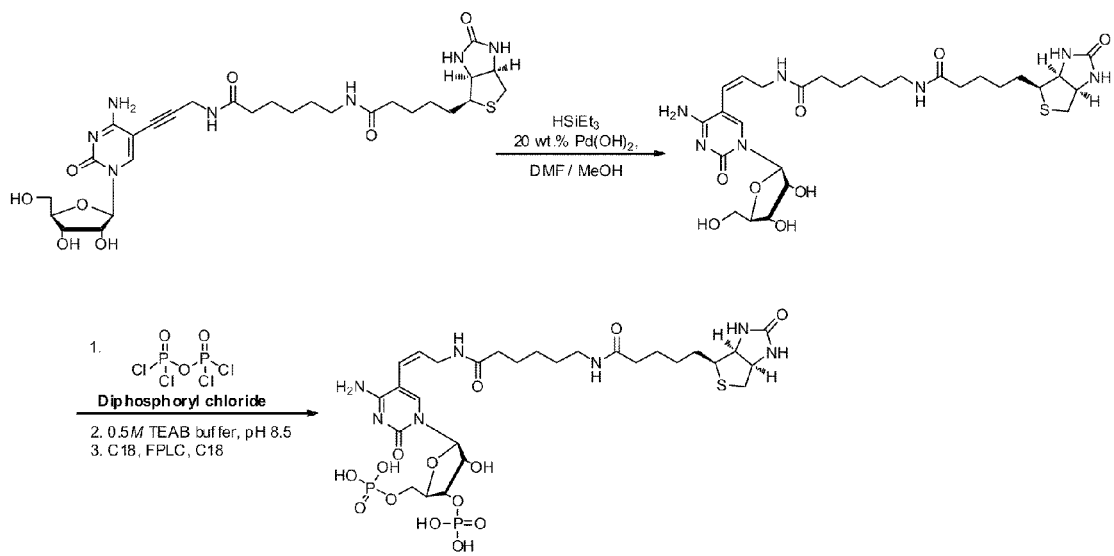
FIG. 3 shows synthesis of biotin-linker-alkene 3',5' cytidine bisphosphate.
Figure 4:
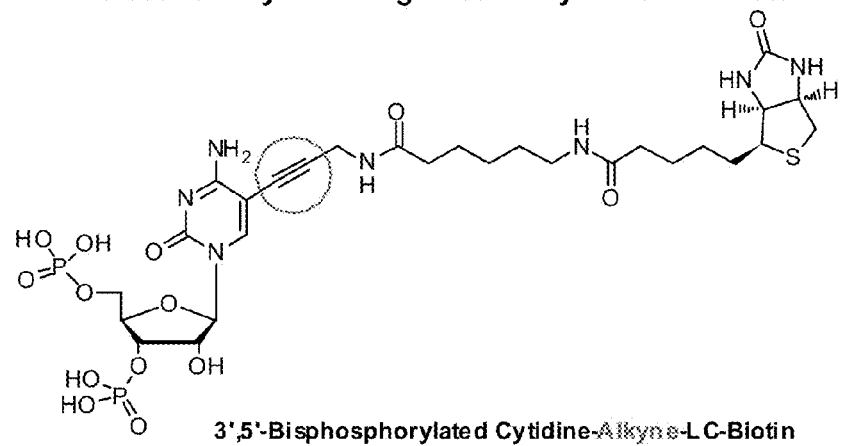
FIG. 4 shows functionality of a modified nucleotide containing an alkyne linkage.
Figure 4:
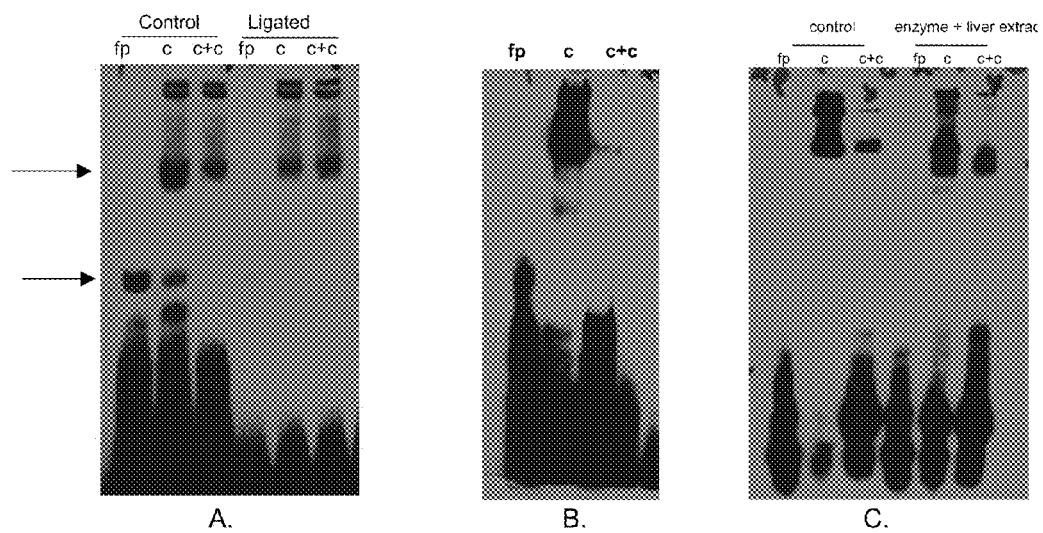
Figure 5:
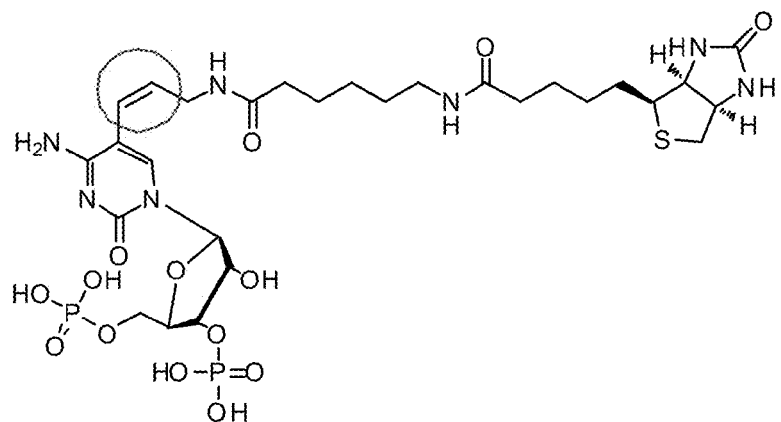
FIG. 5 shows functionality of a modified nucleotide containing an alkene linkage.
Figure 5:
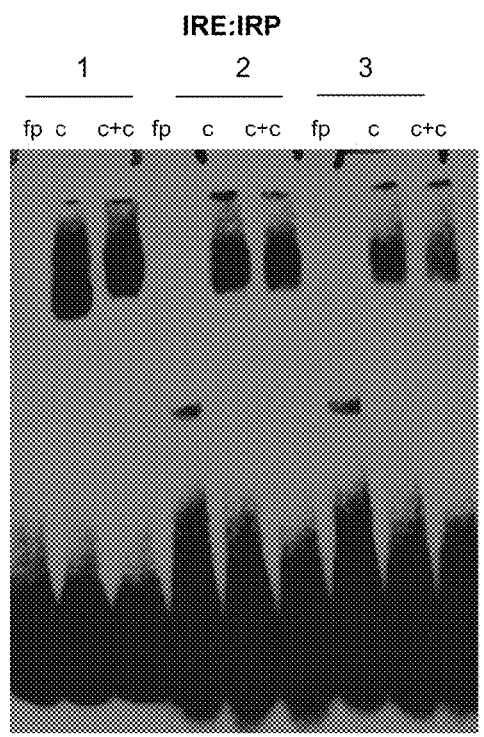
Figure 6:
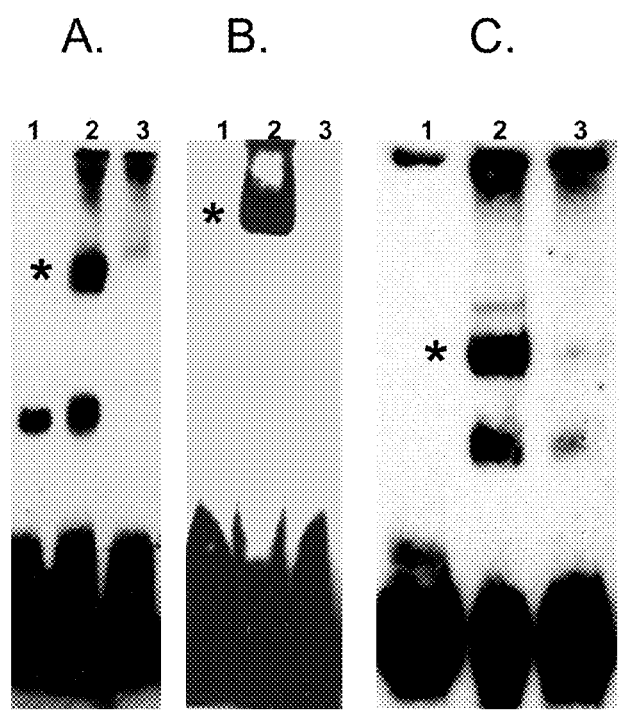
FIG. 6 shows functionality of a modified nucleotide containing an alkane linkage.

In the experiments subsequently described, T4 RNA ligase was used to label RNA with biotinylated cytidine 3',5' bisphosphate. Several molecules were synthesized to optimize the nucleotide for optimal ligation efficiency and functionality, for example, preservation of the interaction of the labeled RNA with other RNA or cellular proteins. Three different alkyl linkages were tested, including alkyne, alkene, and alkane, in combination with both LC (long chain), SC (short chain), and PEG spacers, as shown in FIGS. 1-3. The molecules were tested for ligation efficiency and functionality utilizing established electrophoretic mobility shift (EMSA) controls. In a mobility shift assay, labeled RNA probe is incubated with a cell lysate containing the protein(s) of interest in a binding reaction. The reaction is then electrophoresed on a non-denaturing gel. Unbound probe will migrate to the bottom of the gel, while protein bound probe will migrate more slowly, resulting in a bandshift. The alkyne-LC- and alkyne-SC-containing nucleotides ligated with good efficiency; however, the alkyne linkage was reactive in cell lysates. In a purified system using an RNA polymerase template and purified RNA polymerase, the alkyne compounds produced a functional gel shift (FIG. 4 A), while the alkyne compound did not produce a functional gel shift with the iron responsive element (IRE)—iron responsive protein (IRP) control utilizing cytosolic liver extract (FIG. 4B). When the liver extract was mixed with purified RNA polymerase, the bandshift was affected, suggesting that the alkyne compound is reactive with liver extract (FIG. 4C). Similar results were obtained with the alkene compounds, where the IRE-IRP control ligated, but did not produce a functional bandshift (FIG. 5). The nucleotide containing the alkane linkage and PEG spacer was the most optimal compound for both ligation efficiency and functionality (FIG. 6).

Utilizing the biotin-PEG4-alkane 3,5 cytidine bisphosphate molecule, optimal ligation conditions were determined. The conditions described resulted in ligation efficiencies greater than 70%, and in some cases greater than 90%, depending upon the RNA secondary structure and ligation conditions. A standard reaction had a donor to acceptor ligation ratio of greater than 20:1. The reaction buffer contained 20 U to 40 U T4 RNA ligase, 40 U RNase inhibitor, 50 mM Tris-HCl, 10 mM MgCl$_2$, 10 mM DTT, 1 mM ATP (pH 7.8 at 25° C.), and 15% polyethylene glycol (PEG, MW 20,000). To achieve ligation efficiencies greater than 70%, reactions were incubated at 37° C. for 30 minutes, or at 16° C. from 30 minutes to 24 hours, depending upon the RNA length and secondary structure. In one embodiment, reactions contained 25 pmol to 50 pmol RNA, 1 nmol biotinylated nucleotide, and 20 U to 40 units of T4 RNA ligase in a 30 µl reaction volume. An excess of biotinylated nucleotide did not affect ligation efficiencies, and a range 1 pmol RNA to 200 pmol of RNA was tested in the ligation reaction. The concentration of PEG ranged from 5% to 20%.

As shown in the table below, the ligation conditions were assessed utilizing several RNA species, ranging in length, complexity, and function to demonstrate efficiency of ligation reaction using RNA of varying complexity and length. RNA was derived from the 3' untranslated regions (UTR) of mRNA 28-42 nucleotides, miRNA (22-80 nucleotides), and catalytic RNA (451 nucleotides). RNA was derived synthetically, or from in vitro transcription reactions.

| | Description | RNA source | Length (bases) | Optimal reaction conditions |
|---|---|---|---|---|
| IRE (iron responsive element) | 5' or 3' UTR element | synthetic | 28 | 2 hrs 16 C. |
| RNA polymerase template RNA | RNA | synthetic | 42 | 30 minutes, 37° C. >1 hr 16° C. |
| mir-16-1 | mature micro RNA | synthetic | 22 | ON 16° C. |
| TNF ARE | 3' UTR element | synthetic | 37 | 2 hrs 16° C. |
| Let-7 | pre-miRNA | in vitro transcribed | ~70 | overnight 16° C. |
| hTR | catalytic RNA | in vitro transcribed | 451 | overnight 16° C. |
| COX-76 ARE | 3' UTR element | in vitro transcribed | ~70 | overnight 16° C. |
| mir-16-1 | pre-miRNA | in vitro transcribed | ~70 | overnight 16° C. |

Ligation efficiencies were greater than 70% with reactions using 25-50 pmol RNA, 1 nmol biotinylated nucleotide, 20-40 U T4 RNA ligase, 40 U RNase Inhibitor, 50 mM Tris-HCl, 10 mM MgCl$_2$, 10 mM DTT, 1 mM ATP (pH 7.8 at 25° C.), and 15% PEG (MW 20,000). Ligation efficiencies were improved for RNAs with extensive RNA secondary structure or length by heating briefly before the ligation reaction; heating temperatures ranged from 80° C.-90° C. for 1-5 minutes, followed by rapid-cooling on ice for at least 1 minute to several hours. In some cases, adding 25% DMSO before heating enhanced ligation efficiency. The order of addition of the reaction components did not matter, except for the PEG, which was added last. Several PEG varieties were tested including molecular weights of 1500, 6000, 8500, and 20,000. Although the PEG (MW 20,000) best enhanced ligation efficiency, the other PEG molecules were acceptable, and other size exclusion molecules would also be acceptable. A PEG concentration of 15% was optimal. Other PEG concentrations could also be used, ranging from 5% to 20%.

Ligation efficiencies were assessed using dot blot and quantitative spot densitometry. A synthetically biotinylated RNA was used as a control where 100% biotinylation was assumed. Labeled RNA from the ligation reaction and the synthetically labeled RNA were first normalized to concentration, and then serially diluted to determine efficiency. A small volume was applied (spotted) onto a positively charged nylon membrane. The membrane was cross-linked using ultraviolet (UV) radiation. Biotinylated RNA was detected using a streptavidin horseradish peroxidase (HRP) substrate and chemiluminescent detection. The non-saturating spots, which are spots where the densitometry intensity value was not saturated, were quantitated using densitometry. To determine ligation efficiency, labeled RNA was compared to the control standard to determine efficiency. To determine labeling reproducibility, samples were applied (spotted) in triplicate for two of the RNA samples for intra-assay variability, and each ligation with the optimized conditions was repeated at least three independent times for interassay variability. To determine labeling integrity, labeled RNA was separated by electrophoresis on a gel containing 5% acrylamide/8 M urea (denaturing gel), the RNA was transferred to a nylon membrane and was detected using chemiluminescence. The results indicated that the labeled probes were of high quality, of the correct size, and exhibited either minimal degradation or no degradation.

In vitro transcribed RNA was derived through transcription from a digested plasmid containing the sequence of interest flanked by a T7 polymerase binding site and restriction enzyme site such that only the RNA of interest is transcribed. In vitro transcribed RNA was also derived through transcription of complementary primers containing a T7 RNA polymerase binding sequence element. Digested plasmid was purified by extraction with phenol:chloroform and ethanol precipitation. Complementary primers were annealed in a reaction containing 25 µM of each primer in 10 mM HEPES buffer (pH 7.3). Reactions were incubated at 95° C. for ten minutes followed by slow cooling at room temperature for at least ten minutes, followed by incubation on ice. Transcription reactions typically contained 500 ng-1 µg DNA, 0.5 mM each of ATP, CTP, UTP, and GTP, 1× transcription buffer, 30 U T7 RNA polymerase, and 40 units RNAse inhibitor. Reactions were incubated for 30 minutes to 1 hour at 37° C. DNA was digested for ten minutes with RNAse-free DNAse I at 37° C., followed by inactivation with EDTA. RNA was then selectively precipitated with ethanol, and transcript purity was determined by either agarose or non-denaturing polyacrylamide gel electrophoresis. Precipitated RNA was then quantitated by UV-spectroscopy (absorbance at 260 nm/280 nm), and 25 pmol-50 pmol of RNA was used in each ligation reaction.

The functionality of the labeled RNA was determined by assaying a known interaction of the RNA to ensure that the 3'-end label minimally disturbed secondary structure. Functionality of labeled iron responsive element (IRE), RNA polymerase template, and let-7 micro RNA was determined by RNA electrophoretic mobility shift assay (EMSA). The protein sources included cytosolic liver extract containing iron responsive element-iron responsive protein (IRE-IRP), lin-28 overexpression lysate (let-7-lin28), and purified RNA core polymerase (Epicentre). Dilutions of each RNA (nM) were incubated with the protein of interest in a 1× binding reaction containing 10 mM HEPES (pH 7.3), 20 mM KCl, 1 mM $MgCl_2$, 1 mM DTT, 2.5-10 µg tRNA, and 5% glycerol for 15-30 minutes at room temperature (about 20° C. to about 22° C.). Optimal binding conditions were achieved for RNA polymerase template by substituting tRNA with bovine serum albumin (BSA), and increasing the DTT concentration to 3 mM and the KCl concentration to 40 mM for the let-7-lin28 interaction. Binding reactions composition were separated by electrophoresis on native 6% acrylamide DNA retardation gels for one hr, 100 V, at either room temperature or 4° C. The RNA was then transferred to a positively charged nylon membrane, cross-linked (UV irradiation), and then detected using chemiluminescence. Three binding reactions were assessed for each labeled RNA: 1) migration and intensity of the free probe that migrated toward the bottom of the gel; 2) intensity of the labeled RNA with protein, resulting in a bandshift of the RNA-protein complex; and 3) the competition reaction of the labeled RNA and the unlabeled RNA with protein (FIG. 6). Each bandshift reaction was repeated three times with three independently labeled RNAs. Each of the 3 end-labeled probes was able to functionally bind its respective proteins and produce a robust bandshift, as shown for RNA template-RNA polymerase interaction (FIG. 6A), IRE-IRP interaction (FIG. 6B), and let-7-lin28 interaction (FIG. 6C). Each probe was also functional at the nanomolar level, indicating that the 50 pmol labeling reaction was sufficient for EMSA studies.

In one embodiment, biotin or other suitable moiety, known by one skilled in the art, on the labeled nucleotide serves as an affinity handle for isolating RNA:protein complexes. The functionality of a described biotin-labeled RNA to serve as an affinity handle for isolating RNA complexes (containing RNA, DNA, RNA and DNA, or protein) using an affinity resin, bead, or sensor chip (e.g., pull-down) was determined using streptavidin agarose resin and surface plasmon resonance.

Figure 7:
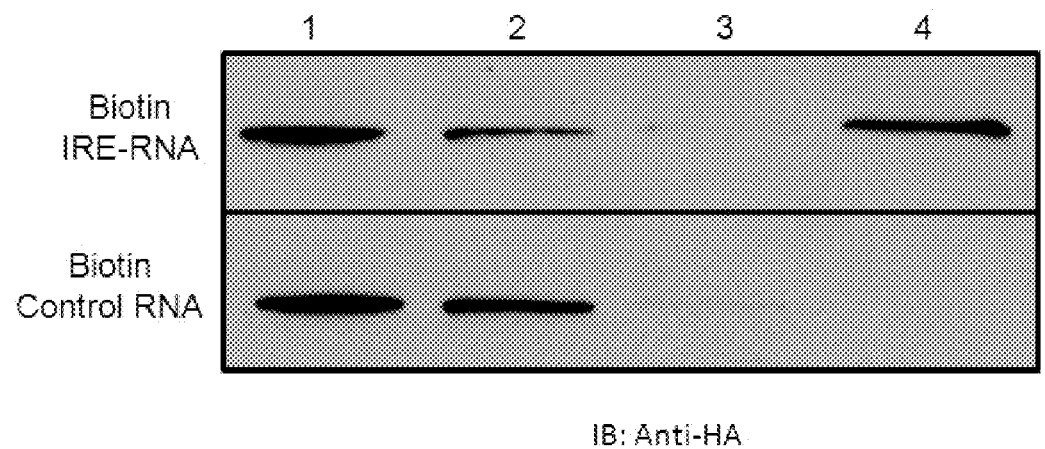
FIG. 7 shows functionality of a modified nucleotide containing an alkane linkage.

IRE-RNA (SEQ ID NO: 1) was labeled using biotinylated cytidine bisphosphate, and T4 RNA ligase. The IRP protein, which binds IRE RNA sequences, was cloned into a vector containing an HA tag and in vitro translated using an human cell-free human in vitro transcription/translation system. Before incubation with the biotinylated RNA, the IRP lysate was incubated with streptavidin agarose resin to reduce non-specific binding, and to remove endogenous biotin. The IRP lysate was then incubated with the labeled IRE, or with a non-specific control RNA (SEQ ID NO: 2) which was 3'-labeled with biotin, in binding buffer (10 mM HEPES pH 7.3, 20 mM KCl, 1 mM $MgCl_2$, 1 mM DTT, 10% glycerol, 40U RNase inhibitor (RNasin®)) for 30 minutes at room temperature, and was then cross-linked with UV light (254 nm) for 10 minutes on ice. Binding reactions were then washed with PBS and the IRE-IRP complex was eluted from the resin. After separation by electrophoresis and transfer to a membrane, IRP was detected using mouse anti-HA antibody. The results are shown in FIG. 7. Lane 1 is 5 µl HA-IRP IVT lysate, lane 2 is 25 µl flow-through fraction, lane 3 is 50 µl wash fraction, and lane 4 is 25 µl eluted fraction.

Figure 8:
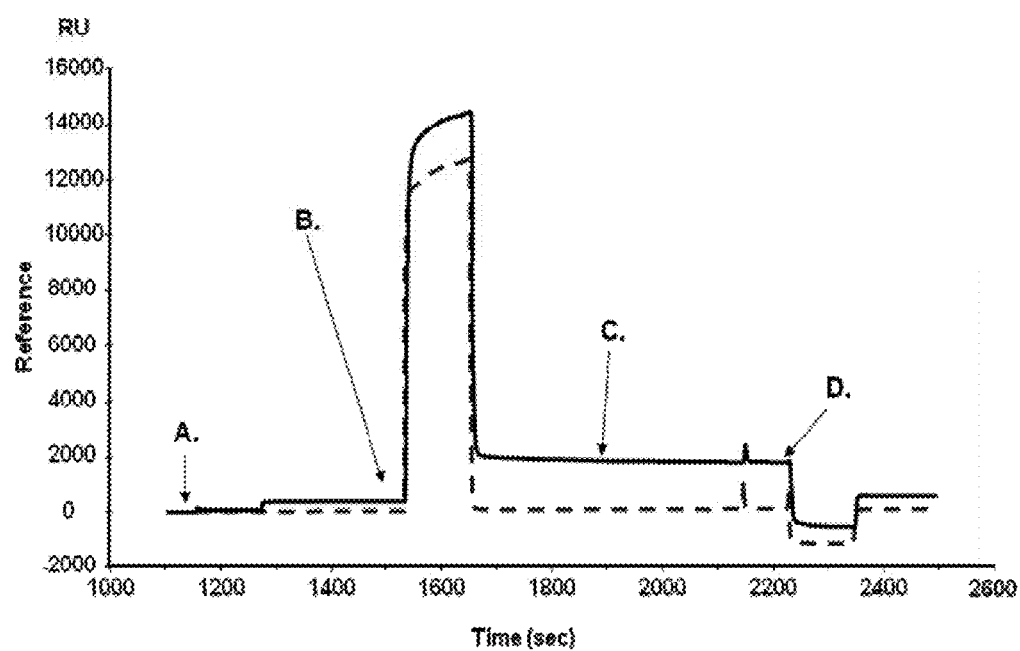
FIG. 8 shows functionality of a modified nucleotide containing an alkane linkage.

The ability of the biotin-labeled RNA to enrich for RNA: protein complexes using an immobilized streptavidin sensor chip was examined using Biacore™ Surface Plasmon Resonance (SPR). The results are shown in FIG. 8 where the solid line is control mRNA and the dashed line is a reference (flow cell 1); and where A=biotinylated RNA template control loading; B=RNA Pol II injection; C=RNA Pol II bound to control RNA; and D=injection of unlabeled control RNA. Biotin-labeled control RNA was captured on a Streptavidin-coated sensor chip followed by injection of bacterial RNA Polymerase. A binding response of RNA polymerase II was detected on the active RNA surface and specificity was confirmed by the loss of binding after injection of non-labeled control RNA. Twenty pmol labeled RNA was diluted into nuclease-free HEPES buffer (pH 7.3), injected at 5 µl/min for four minutes, and captured onto a commercially purchased streptavidin-coated sensor chip for the Biacore 3000®. Bacterial RNA polymerase (0.1 U/µl) was then injected for two minutes. As shown in FIG. 8, a binding response of RNA polymerase II was detected on the active RNA surface and specificity was confirmed by loss of binding after injecting non-labeled control RNA. Specificity was determined through competition of binding RNA polymerase with a 50-100 fold excess of non-labeled RNA polymerase template RNA that was injected for four minutes.

One embodiment is a method to assay RNA using an RNA probe labeled with the compound described above and using the method described above. The labeled RNA can be synthesized as described above. The labeled RNA probe is contacted with the sample to be assayed under conditions to permit the labeled RNA to hybridize with RNA in the sample and to detect the hybridization in an assay, e.g., mobility shift, Northern blot, in situ hybridization, pull-down assay, etc. using, e.g., a streptavidin-conjugated reporter molecule such as an enzyme, a fluorescent compound, an isotope, a gold particle, etc.

The embodiments shown and described in the specification are only specific embodiments of inventors who are skilled in the art and are not limiting in any way. Therefore, various changes, modifications, or alterations to those embodiments may be made without departing from the spirit of the invention in the scope of the following claims.

Applicants incorporate by reference the material contained in the accompanying computer readable Sequence Listing identified as SEQ_ST25.txt, having a file creation date of Mar. 25, 2011 and file size of 680 bytes.

Alk is a connecting group having the structure —//—$(CH_2)_m$—Y—//— where Y is a bond or bond forming group selected from

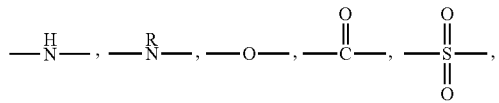

and $m$ is an integer ranging from 3 to 6 inclusive, and wherein the leftmost bond is to Nus and the rightmost bond is to Lnk;

Lnk is a linking group having the structure

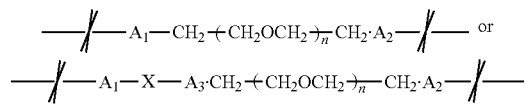

where $n$ is an integer ranging from 2 to 48 inclusive;

What is claimed is:

1. A compound having the structure (I):

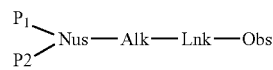

(I)

or a salt, conjugate base, tautomer, or ionized form thereof, wherein

P1 is a phosphate group;

P2 is a phosphate group;

Nus is a nucleoside moiety comprising a sugar bound to a purine or pyrimidine base;

$A_1$ is a bond forming group selected from

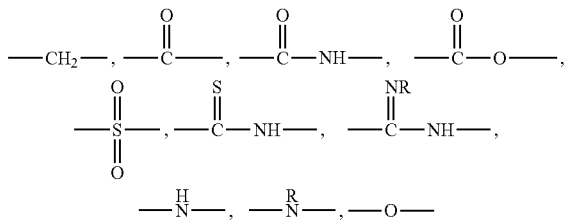

$A_2$ is a bond forming group selected from

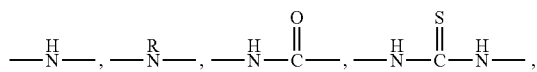

-continued

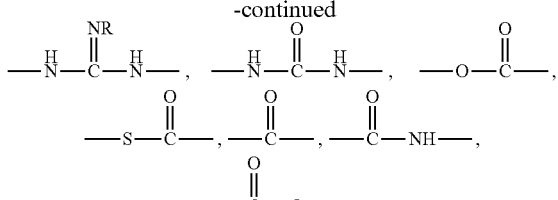

A₃, when present, is a bond forming group selected from

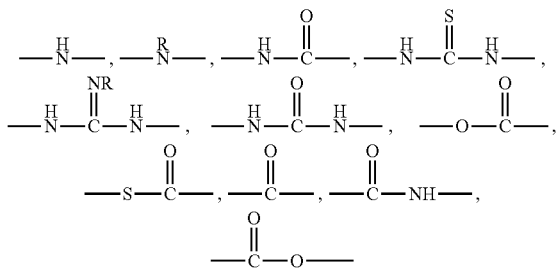

and X is a cleavable group that can undergo silicon-carbon cleavage, nucleophilic cleavage, redox cleavage, photochemical cleavage, enzymatic cleavage, or exchange-based cleavage, and the leftmost bond is to Alk and the rightmost bond is to Obs; and Obs is an observable label.

2. The compound of claim 1 wherein
the sugar is ribose having a 5' site, a 3' site, and a 1' site,
P1 is attached to ribose at the 5' site, P2 is attached to ribose at the 3' site,
and the purine or pyrimidine base is selected from cytosine (C), uracil (U), adenine (A), guanine (G), or inosine (I) and is attached to ribose at the 1' site.

3. The compound of claim 1 wherein the purine or pyridine base is selected from 1-methyladenine, N6-methyladenine, N6-isopentyladenine, N,N-dimethyladenine, 7-deazaadenine, 2-thiocytosine, 3-methylcytosine, N4-acetylcytosine, 2-thiocytosine, 1-methylguanine, 2-methylguanine, 7-methylguanine, N2,N2-dimethylguanine, 7-deazaguanine, 2-thiouracil, 6-thiopurine, or 2,6-diaminopurine.

4. The compound of claim 1 wherein the observable label is a chromogen, a fluorophore, a mass label, a spin label, a streptavidin-binding label, or a secondary detection label.

5. The compound of claim 1 wherein n is an integer ranging from 2 to 24 inclusive.

6. The compound of claim 1 wherein the sugar is ribose, the purine or pyrimidine base is selected from adenine (A), cytosine (C), guanine (G), uracil (U), or inosine (I), m is 3, n is 4, and the observable label is a streptavidin-binding compound selected from biotin, desthiobiotin, or iminobiotin.

7. The compound of claim 1 wherein the sugar is ribose, the purine or pyrimidine base is cytosine (C),
m is 3, Lnk is

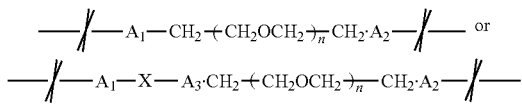

wherein n is 4,
A₂ is

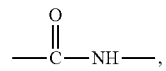

A₂ is

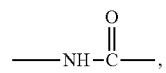

and when present, A₃ is

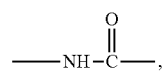

and Obs is selected from the group consisting of biotin, a fluorophore, and an azide.

8. A method of labeling a ribonucleic acid (RNA), the method comprising
heating RNA in a solution, the solution optionally containing dimethylsulfoxide at a concentration up to 25%, to at least 75° C. up to 95° C. then cooling the heated RNA for at least one minute to less than 10° C., and,
contacting the heated and cooled RNA with the compound of claim 1 under reaction conditions using T4 RNA ligase and including PEG having molecular weight between about 1500 and 24,000 inclusive and at a concentration ranging from 5% PEG to 20% PEG inclusive to ligate the compound of claim 1 to the RNA to result in a modified RNA.

9. The method of claim 8 wherein the concentration of PEG is about 15%.

10. The method of claim 8 wherein the molecular weight of PEG is 20,000.

11. The method of claim 8 using the compound of claim 1.

12. A method of synthesizing the compound of claim 1, wherein the compound is biotin-polyethylene glycol (PEG)-alkane-3',5'-cytidine-bisphosphate, the method comprising
reacting propargyltrifluoroacetamide with 5-iodocytidine to result in 5-[3-(trifluoroacetamido)propynyl]cytidine,
converting 5-[3-(trifluoroacetamido)propynyl]cytidine to 5-[3-(trifluoroacetamido)propyl]cytidine, converting 5-[3-(trifluoroacetamido)propyl]cytidine to 5-(3-aminopropyl)cytidine,
reacting 5-(3-aminopropyl)cytidine with NHS-PEG-biotin to result in biotin-PEG-alkane-cytidine,
and
reacting biotin-PEG-alkane-cytidine with diphosphoryl chloride to result in biotin-polyethylene glycol (PEG)-alkane-3',5'-cytidine-bisphosphate.

13. A kit comprising the compound of claim 1 and instructions for labeling a ribonucleic acid (RNA) with the compound.

14. A kit comprising the compound of claim 1, wherein Obs is biotin, and instructions for capturing and/or using a ribonucleic acid (RNA) labeled with the compound on an array or chip.

15. A method for assaying a ribonucleic acid (RNA) analyte, the method comprising
  labeling an RNA with the compound of claim 1 to result in a modified RNA probe, and
  contacting the modified RNA probe with a sample containing the RNA analyte under conditions to hybridize the modified RNA probe with the RNA analyte, and
  detecting the RNA analyte hybridized with the modified RNA probe, wherein hybridization and detection of the modified RNA probe assays the RNA analyte.

16. The method of claim 15 where the assay is at least one of mobility shift, Northern blot, pull-down assay, or in situ hybridization.

17. The method of claim 15 where the detection uses a streptavidin-conjugated reporter molecule.

18. The method of claim 15 where the reporter molecule is selected from the group consisting of enzymes, fluorescent compounds, isotopes, gold particles, and combinations thereof.

19. The method of claim 15 using the compound of claim 1.

20. A compound having the structure

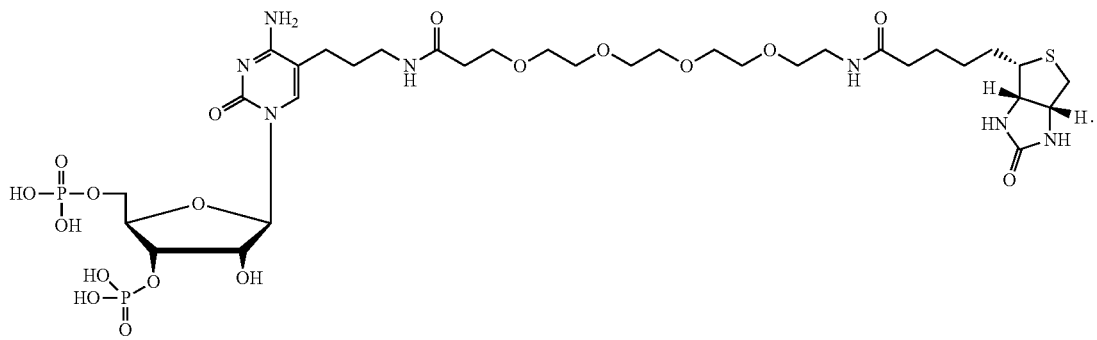

* * * * *

UNITED STATES PATENT AND TRADEMARK OFFICE
CERTIFICATE OF CORRECTION

PATENT NO. : 8,536,323 B2  Page 1 of 1
APPLICATION NO. : 13/090729
DATED : September 17, 2013
INVENTOR(S) : Opperman et al.

It is certified that error appears in the above-identified patent and that said Letters Patent is hereby corrected as shown below:

In the Claims:

- Column 54, Claim 1, Line 65 reads "[chemical structures]"

it should read -- [chemical structures] --

- Column 55, Claim 1, Line 15 reads "[chemical structures]"

it should read -- [chemical structures] --

- Column 56, Claim 7, Line 2 reads "$A_2$ is"
    it should read --$A_1$ is--

Signed and Sealed this
Twenty-ninth Day of October, 2013

Teresa Stanek Rea
*Deputy Director of the United States Patent and Trademark Office*